(12) United States Patent
Le et al.

(10) Patent No.: US 10,539,731 B2
(45) Date of Patent: Jan. 21, 2020

(54) GRIN LENS AND METHODS OF MAKING THE SAME

(75) Inventors: Anthony Van Le, San Jose, CA (US); Nicholas John Richardi, Manteca, CA (US)

(73) Assignee: Poinare Systems, Inc., Menlo Park, CA (US)

( * ) Notice: Subject to any disclaimer, the term of this patent is extended or adjusted under 35 U.S.C. 154(b) by 0 days.

(21) Appl. No.: 13/491,530

(22) Filed: Jun. 7, 2012

(65) Prior Publication Data

US 2013/0331709 A1    Dec. 12, 2013

(51) Int. Cl.
*A61B 6/00* (2006.01)
*F21V 8/00* (2006.01)
*G02B 6/32* (2006.01)
*A61B 5/00* (2006.01)

(52) U.S. Cl.
CPC .......... *G02B 6/0008* (2013.01); *A61B 5/0066* (2013.01); *A61B 5/0084* (2013.01); *G02B 6/32* (2013.01)

(58) Field of Classification Search
CPC .......... G02B 3/0087; G02B 5/00; G02B 6/00; G02B 6/255; G02B 2006/02
USPC .................................. 600/473, 476, 478–479
See application file for complete search history.

(56) References Cited

U.S. PATENT DOCUMENTS

| 5,567,363 | A | * | 10/1996 | Jung et al. ..................... 264/2.6 |
| 6,129,667 | A | * | 10/2000 | Dumoulin .......... A61B 1/00183 600/424 |
| 6,226,432 | B1 | * | 5/2001 | Gonda ............... G02B 23/2476 385/115 |
| 6,236,506 | B1 | * | 5/2001 | Cao .......................... 359/484.05 |
| 6,445,939 | B1 | * | 9/2002 | Swanson et al. ............. 600/342 |
| 6,564,087 | B1 | * | 5/2003 | Pitris .................. A61B 1/00183 600/478 |
| 2003/0004412 | A1 | * | 1/2003 | Izatt et al. ..................... 600/425 |
| 2003/0032204 | A1 | * | 2/2003 | Walt et al. ..................... 436/518 |
| 2006/0138238 | A1 | * | 6/2006 | Johnston et al. ........ 235/462.32 |

OTHER PUBLICATIONS

Mao et al (Fiber lenses for ultra-small probes used in optical coherent tomography).*

* cited by examiner

*Primary Examiner* — Joel F Brutus
(74) *Attorney, Agent, or Firm* — Vista IP Law Group, LLP

(57) ABSTRACT

An imaging device includes a grin lens having a proximal end and a distal end, wherein the grin lens is made from a polymeric material, an optical fiber having a distal end coupled to the proximal end of the grin lens, and a beam director coupled to the distal end of the grin lens, wherein the beam director is configured to direct light at an angle relative to a longitudinal axis of the optical fiber.

18 Claims, 23 Drawing Sheets

GRIN LENS AND METHODS OF MAKING THE SAME

FIELD

This application generally relates to medical imaging, and more specifically, to systems and methods for rotational scanning of internal bodily structures.

BACKGROUND

Imaging devices may be used to perform imaging at internal region of a human body. Optical coherence tomography (OCT) is an imaging technique that involves scanning a light beam to gather image signals of a target region.

Applicant of the subject application determines that it would be desirable to have a new imaging device with a rotating optical waveguide.

SUMMARY

In accordance with some embodiments, an imaging device includes a grin lens having a proximal end and a distal end, wherein the grin lens is made from a polymeric material, an optical fiber having a distal end coupled to the proximal end of the grin lens, and a beam director coupled to the distal end of the grin lens, wherein the beam director is configured to direct light at an angle relative to a longitudinal axis of the optical fiber.

In one or more embodiments, the grin lens and the optical fiber are secured relative to each other by an adhesive.

In one or more embodiments, the grin lens and the optical fiber are secured relative to each other by fusion splicing.

In one or more embodiments, the imaging device further includes a spacer disposed between the distal end of the optical fiber and the grin lens, wherein the distal end of the optical fiber is indirectly coupled to the proximal end of the grin lens.

In one or more embodiments, the grin lens and the optical fiber are secured relative to each other by a ferrule.

In one or more embodiments, the ferrule comprises a first lumen for housing the distal end of the optical fiber, and a second lumen for housing at least a part of the grin lens.

In one or more embodiments, the ferrule is made from an adhesive disposed around the distal end of the optical fiber, around at least a part of the grin lens, or around both.

In one or more embodiments, the imaging device further includes a tube surrounding the optical fiber.

In one or more embodiments, a distal portion of the ferrule has a cross sectional dimension that is larger than a cross sectional dimension of the tube.

In one or more embodiments, a distal portion of the ferrule has a cross sectional dimension that is a same as a cross sectional dimension of the tube.

In one or more embodiments, a distal portion of the ferrule has a cross sectional dimension that is less than a cross sectional dimension of the tube.

In one or more embodiments, the imaging device further includes a housing coupled to the grin lens, the housing surrounding the beam director and having an optical port.

In one or more embodiments, the distal end of the optical fiber has a cross sectional dimension that is larger than a cross sectional dimension of a proximal section of the optical fiber.

In one or more embodiments, the imaging device further includes a tube surrounding the optical fiber, the tube being a part of a rotational shaft.

In one or more embodiments, the grin lens has a cross sectional dimension that is a same as a cross sectional dimension of the tube.

In one or more embodiments, the grin lens has a cross sectional dimension that is larger than a cross sectional dimension of the tube.

In one or more embodiments, the grin lens has a cross sectional dimension that is less than a cross sectional dimension of the tube.

In one or more embodiments, the tube comprises a plurality of cutouts.

In one or more embodiments, the grin lens is configured to perform light collimation and light focusing.

In other embodiments, the imaging device may be a part of an OCT system, which includes a catheter body, wherein the optical fiber is configured to rotate in a lumen within the catheter body.

In other embodiments, an imaging device includes a grin lens having a proximal end for coupling to an optical fiber, and a distal end for coupling to a beam director, wherein the grin lens is made from a polymeric material, and wherein the grin lens is configured to perform light collimation and light focusing.

In some embodiments, an imaging device includes a grin lens having a proximal end and a distal end, an optical fiber having a distal end coupled to the proximal end of the grin lens, a tube surrounding the optical fiber, wherein the tube is coupled to the optical fiber and includes a plurality of cutouts, and a beam director coupled to the distal end of the grin lens, wherein the beam director is configured to direct light at an angle relative to a longitudinal axis of the optical fiber.

In one or more embodiments, the imaging device further includes a clad layer disposed between the optical fiber and the tube.

In one or more embodiments, the tube is a part of an optical cable that includes the optical fiber.

In one or more embodiments, the imaging device further includes a clad layer surrounding the optical fiber, and a material surrounding the clad layer, wherein the tube surrounds the material.

In one or more embodiments, the tube is frictionally engaged with the sleeve.

In one or more embodiments, the tube is secured to the sleeve via an adhesive.

In one or more embodiments, the material comprises one or more layers disposed between the clad layer and the tube.

In one or more embodiments, the grin lens is made from a polymeric material.

In one or more embodiments, the tube has a torsional stiffness that is at least 0.00001 newton/meter2.

In one or more embodiments, the tube has an axial stiffness that is at least 0.001 newtons.

In one or more embodiments, a distal section of the tube has a bending stiffness that is at most 70000000 newton/meter2.

In one or more embodiments, the tube has a torsional stiffness that is at least 0.00001 newton/meter2, the tube has an axial stiffness that is at least 0.001 newtons, and a distal section of the tube has a bending stiffness that is at most 70000000 newton/meter2.

In one or more embodiments, the tube has a cross sectional dimension that is less than 1000 um.

In one or more embodiments, the tube has a cross sectional dimension that is less than 600 um.

In one or more embodiments, the tube has a cross sectional dimension that 400 um or less.

In one or more embodiments, one of the cutouts has an elongate configuration with an axis that is perpendicular to a longitudinal axis of the tube.

In one or more embodiments, one of the cutouts has an elongate configuration with an axis that forms a non-perpendicular angle relative to a longitudinal axis of the tube.

In one or more embodiments, one of the cutouts has a circular shape.

In one or more embodiments, one of the cutouts has a sinusoidal shape.

In one or more embodiments, the cutouts comprise rows and columns of circular openings.

In one or more embodiments, the cutouts comprise rows and columns of rectangular openings.

In one or more embodiments, the cutouts are staggered.

In one or more embodiments, the cutouts are non-staggered.

In one or more embodiments, the imaging device of claim 1 is a part of an OCT system, which includes a catheter body, wherein the tube is configured to rotate in a lumen within the catheter body.

Other and further aspects and features will be evident from reading the following detailed description of the embodiments.

BRIEF DESCRIPTION OF THE DRAWINGS

The drawings illustrate the design and utility of embodiments, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only typical embodiments and are not therefore to be considered limiting of its scope.

DESCRIPTION OF THE EMBODIMENTS

Figure 1:
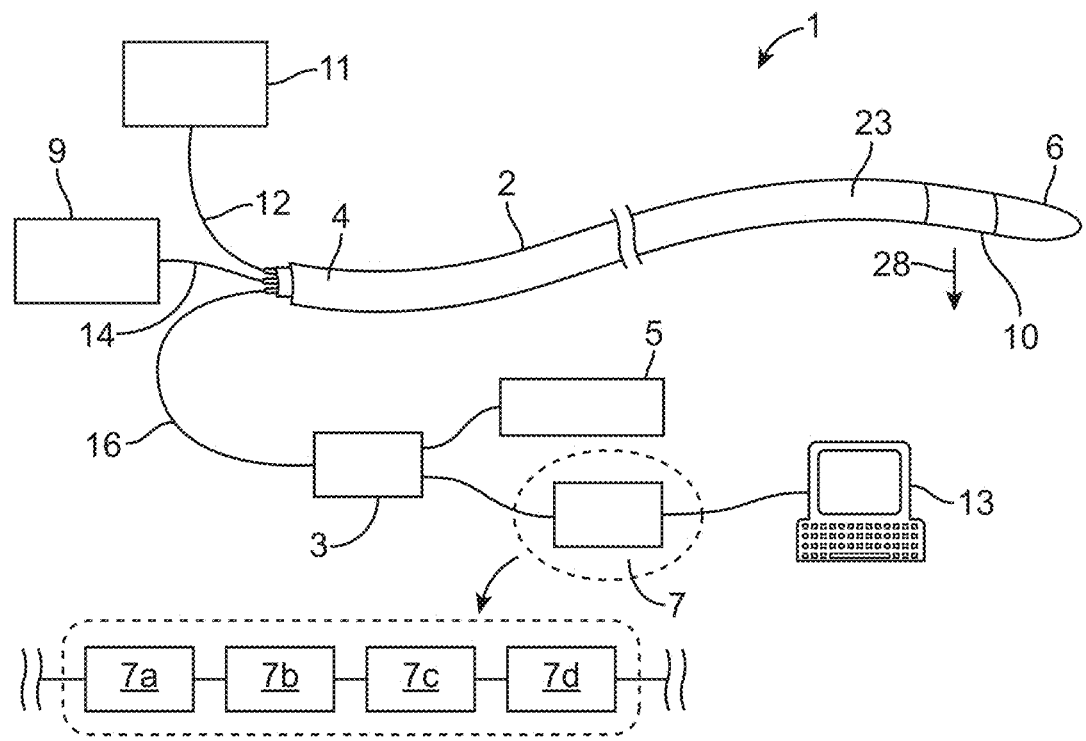
FIG. 1 illustrates an imaging probe in accordance with some embodiments.

Various embodiments are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated.

Referring to FIG. 1, an imaging device 1 is shown in accordance with some embodiments. The imaging device 1 will be described as an imaging probe 1. However, it should be understood that the imaging device 1 may have other configurations, and may not be in a form of a probe. The imaging probe 1 may have an outer dimension that is anywhere between 50 micron to 50 mm, and more preferably, between 0.5 mm to 10 mm, and even more preferable between 0.2 mm to 1.5 mm (such as 1 mm). Thus, the imaging probe 1 may be placed at different regions inside a body to obtain images. By means of non-limiting examples, the regions may include the aorta, colon, ear canal, esophagus, fallopian tube, blood vessel (vein, artery), passage way in a lung, etc. In other embodiments, the imaging probe 1 may have other outer dimensions that are different from the ranges described above.

In different embodiments, the imaging probe 1 may be configured to perform different types of imaging, such as optical coherence tomography (also known as optical frequency domain imaging), mulitphoton imaging, confocal imaging, Raman spectroscopy, spectroscopy, scanning imaging spectroscopy, and Raman spectroscopic imaging. In other embodiments, the imaging probe 1 may perform other types of imaging.

The imaging probe 1 has an elongated tube 2 with a proximal end 4, a distal end 6, and a body 23 extending between the proximal end 4 and the distal end 6. The imaging probe 1 also has a transparent region 10 located between the proximal end 4 and the distal end 6 such that a focused light beam 28 can pass therethrough from inside the imaging probe 1 in a radial direction to perform an image scanning. The region 10 may have an arc or ring configuration, which allows the beam 28 to exit through the region 10 at different angular positions. The region 10 also allows light (e.g., light provided from the probe 1 and reflected from a tissue) from outside the imaging probe 1 to enter into the imaging probe 1. The region 10 may be completely transparent in some embodiments. In other embodiments, the region 10 may be partially transparent, as long as it can allow some light to pass therethrough in both directions. The imaging probe 1 also includes a fluid connection 12, an electrical connection 14, and an optical connection 16, all located at the proximal end 4.

The fluid connection 12 is configured to couple to a fluid source 11 (such as a saline filled syringe or IV bag) to provide for fluid for flushing the distal end of the imaging probe 1 during use. In such cases, the distal end of the imaging probe 1 may include a flush port in fluid communication with the fluid connection 12. The flush port may aim at the transparent region 10 of the imaging probe 1. In other embodiments, the fluid may be ringers lactate solution, radio-opaque fluid (such as Visopaque™) or other agent. During imaging, there may be blood flow, and the blood cells may scatter the light, and/or may act as little particles that block the light beam, causing the image quality to drop down significantly. The flush port is advantageous because it allows the distal end of the imaging probe 1 to be cleaned during use. In other embodiments, the fluid connection 12 may be in fluid communication with a lumen in the imaging probe 1. In such cases, the fluid source 11 may provide fluid through the connection 12 to flush fluid to clear the lumen, and/or to partially or completely dilute blood to reduce light scattering caused by blood cells thereby allowing capture of higher quality images. In further embodiments, the fluid connection 12 may be connected to a suction device, which provides a vacuum suction for aspiration to suck materials (e.g., fluid, object, etc.) out of the lumen. The fluid connection 12 is illustrated as being on the probe 1, but in other embodiments, the fluid connection 12 may be on a sheath that surrounds the probe 1.

In the illustrated embodiments, the imaging probe 1 is a part of an imaging system that includes a module 3 comprising of an interferometer, a laser source 5, a processing module 7, and a user interface 13. In other embodiments, any one or a combination of the components 3, 5, 7, and 13 may be considered component(s) of the imaging probe 1. The module 3 is optically coupled to the imaging probe 1 through the optical connection 16 during use. The laser source 5 is configured to provide a broadband or narrowband input light to the module 3. In the illustrated embodiments, the input light is in an infrared range. In some embodiments, the input light has a center wavelength that is anywhere between 100 nm and 11000 nm, and more preferably, anywhere between 1000 nm and 2000 nm, and even more preferably anywhere between 1100 nm and 1600 nm (such as 1310 nm). In other embodiments, the input light may have other wavelengths. The module 3 passes the input light to an optical waveguide that transmits the input light to the inside of the imaging probe 1. The input light is processed optically (e.g., focused, collimated, reflected, etc.) inside the imaging probe 1, and the processed input light is output through region 10 of the imaging probe 1 as an output light. In the illustrated embodiments, the output light has a wavelength that is anywhere between 100 nm and 11000 nm, and more preferably anywhere between 500 nm and 1500 nm, and even more preferably anywhere between 1200 nm and 1400 nm (such as 1310 nm). In other embodiments, the output light may have other wavelengths. It should be noted that the term "light" or similar terms (such as "light beam") is not limited to non-visible light, and may refer to any radiation in different wavelengths, which may or may not be visible.

The output light from the imaging probe 1 impinges onto a tissue within a patient, and is reflected from the tissue. The reflected light from the tissue is then captured by the probe 1 through region 10, is optically processed inside the imaging probe 1, and is then transmitted by the optical waveguide back to the module 3. The module 3 passes the light signal from the probe 1 to the processing module 7. The processing module 7 detects and processes the signal, and transmits it to the user interface 13. In the illustrated embodiments, the processing module 7 includes one or more photodetector(s) 7a, a signal amplifier or conditioner with an ant-alias filter 7b, an ND converter 7c, and a Fast Fourier Transform (FFT) processor 7d. The photodetector(s) 7a is configured to detect light containing the depth encoded interferogram from module 3, and convert the light to electrical signal(s). The electrical signals are further conditioned and amplified by the component 7b to be suitable for use by the A/D converter 7c. Once the signal is converted from the analog domain to digital domain by the A/D converter 7c, the FFT processor 7d converts the depth encoded electrical interferogram signal via FFT to a depth resolved signal for each point scanned by the imaging probe 1. The FFT processor 7d maybe a discrete processing board, or maybe implemented by a computer. The user interface 13 may be a computer (as illustrated), a hand-held device, or any of other devices that is capable of presenting information to the user. The user interface 13 reconstructs the image from the FFT processor 7d and display a result (e.g., an image) of the processing in a screen for the user's viewing.

The delivering of output light by the imaging probe 1, and the receiving of reflected light by the imaging probe 1, may be repeated at different angles circumferentially around the probe 1, thereby resulting in a circumferential scan of tissue that is located around the imaging probe 1. In some embodiments, one or more components within the distal end of the probe 1 are configured to rotate at several thousand times per minute, and the associated electronics for processing the light signals are very fast, e.g., has a sample rate of 180,000,000 times a second. In other embodiments, the one or more components within the distal end of the probe 1 may rotate at other speeds that are different from that described previously. Also, in other embodiments, the associated electronics for processing the light signals may have a data processing speed that is different from that described previously.

The electrical connection 14 may be used to control functions of the imaging probe 1, as well a providing power to magnetic coils to turn a rotor that is in, or coupled to, the probe 1. In some embodiments, the electrical connection 14 may be connected to one or more sensors to sense position, velocity, acceleration, jerk, etc., of a rotor that is in, or coupled to, the probe 1.

The imaging system also includes a control 9 electrically coupled to the imaging probe 1 through the electrical connection 14. In some embodiments, the control 9 may be used to control a positioning of one or more optical components located inside the imaging probe 1. For example, in some embodiments, the control 9 may have a manual control for allowing a user to control a turning (e.g., amount of turn, speed of turn, angular position, etc.) of a beam director (e.g., a mirror or a prism) which directs the light beam 28 to exit through the region 10 at different angles.

In other embodiments, the control 9 may having a manual control for allowing a user to move one or more lens inside the imaging probe 1 so that a focusing function may be performed. In further embodiments, the control 9 may have a switch which allows a user to select between manual focusing, or auto-focusing. When auto-focusing is selected, the imaging system will perform focusing automatically.

In still further embodiments, the control 9 may also includes one or more controls for allowing a user to operate the imaging probe 1 during use (e.g., to start image scanning, stop image scanning, etc.).

In further embodiments, the imaging probe 1 is flexible and is steerable using the control 9. For example, the imaging probe 1 may be implemented as a steerable catheter. In such cases, the imaging probe 1 may include a steering mechanism for steering the distal end 6 of the imaging probe 1. For example, the steering mechanism may include one or more wires coupled to the distal end 6 of the imaging probe 1, wherein tension may be applied to any one of the wires using the control 9. In particular, the control 9 may include a manual control that mechanically couples to the wire(s). During use, the user may operate the manual control to apply tension to a selected one of the wires, thereby resulting in the distal end 6 bending in a certain direction.

Figure 1A:
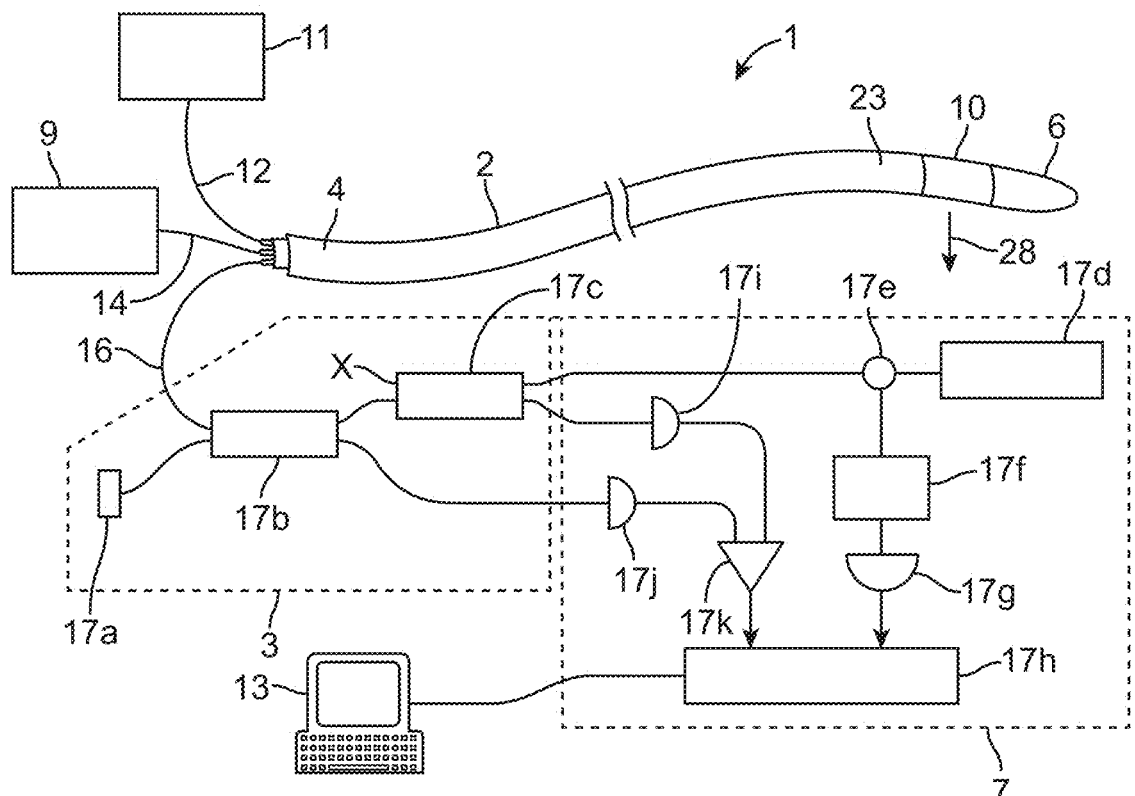
FIG. 1A illustrates an imaging probe in accordance with other embodiments.

The imaging probe 1 may be implemented using different devices and/or techniques. FIG. 1A illustrated an example of how the components 3, 7 of the imaging probe 1 may be implemented in accordance with some embodiments. In the illustrated embodiments, the module 3 includes optical waveguide (e.g., fiber optic) couplers 17b and 17c forming an interferometer. Reference mirror 17a is connected to reference arm of the interferometer, while the sample arm of the interferometer is connected to the imaging probe 1 through connection 16. Light from laser 17d is transmitted to a splitter 17e, which divides a portion of the light from the laser 17d for transmission to the module 3, while the other portion of the light is diverted to a reference clock interferometer 17f. At the module 3, the light from the laser 17d is received at the coupler 17c, and is then transmitted to the coupler 17b, wherein part of the light is passed to the reference mirror 17a, and the rest is passed to the imaging probe 1. The light at the reference mirror 17a is reflected back to the coupler 17b, which divides the light so that a portion of it goes to the coupler 17c and to the photo detector 17i, and another portion of it goes to the photo detector 17j. The light delivered to the probe 1 exits from the region 10 of the imaging probe 1 and strikes a sample. The imaging probe 1 then detects the reflected light back from the sample, and optically communicates the reflected light through imaging probe 1 and module 3, where the path length difference creates an interferogram containing the depth encoded information which is detected by photo detectors 17i and 17j. In particular, the light from the sample is transmitted to the coupler 17b, which divides the light so that a portion of it goes to the coupler 17c and to the photo detector 17i, and another portion of it goes to the photo detector 17j. Photodetectors 17i and 17j are optically communicated to module 3 and are configured for providing balanced signal detection using differential amplifier 17k. Thus, for every light signal provided by the source 17d, the differential amplifier 17k receives a reflected from the reference mirror 17a, and another signal from the light sampled at the distal end of the probe 1. The signal from the differential amplifier 17k is then digitized by the A/D converter 17h. Reference clock interferometer 17b is optically communicated to photo detector 17g to covert the optical clocking signals to electrical signals. In the illustrated embodiments, the interferometer 17f may be implemented using a Fabry Perot interferometer or Mach-Zehnder interferometer. In other embodiments, the interferometer 17f may be implemented using other devices. The electrical clocking signals from 17g are used to provide the clocking signal in even wavenumber space for the A/D converter 17h, which digitizes the analog signals and converts them into the digital domain for further processing. In the illustrated embodiments, the user interface 13 includes a computer, which may be used to perform FFT on the signals from the A/D converter 17h. The computer then reconstructs one or more images for display at a screen of the user interface 13. In some embodiments, the user interface 13 reconstructs the images by placing the processed signals from FFT into a rectangular array, which is then mapped to polar coordinates representing the radial scan performed by the imaging probe 1. The data is then compressed logarithmically to compress the dynamic range of the signal such that it is easily perceived by the user, which is then displayed as an intensity mapped image showing the fully reconstructed image for the user to view. The computer may also be used to perform further signal processing and/or image processing, if desired. Alternatively FFT, signal processing, and/or image reconstruction may be performed using a separate module(s) or device(s). The image(s) at the user interface 13 may then be used for diagnostic and/or treatment purposes. It should be noted that the imaging probe 1 is not limited to the example illustrated, and that in other embodiments, the imaging probe 1 may have different configurations.

Figure 1B:
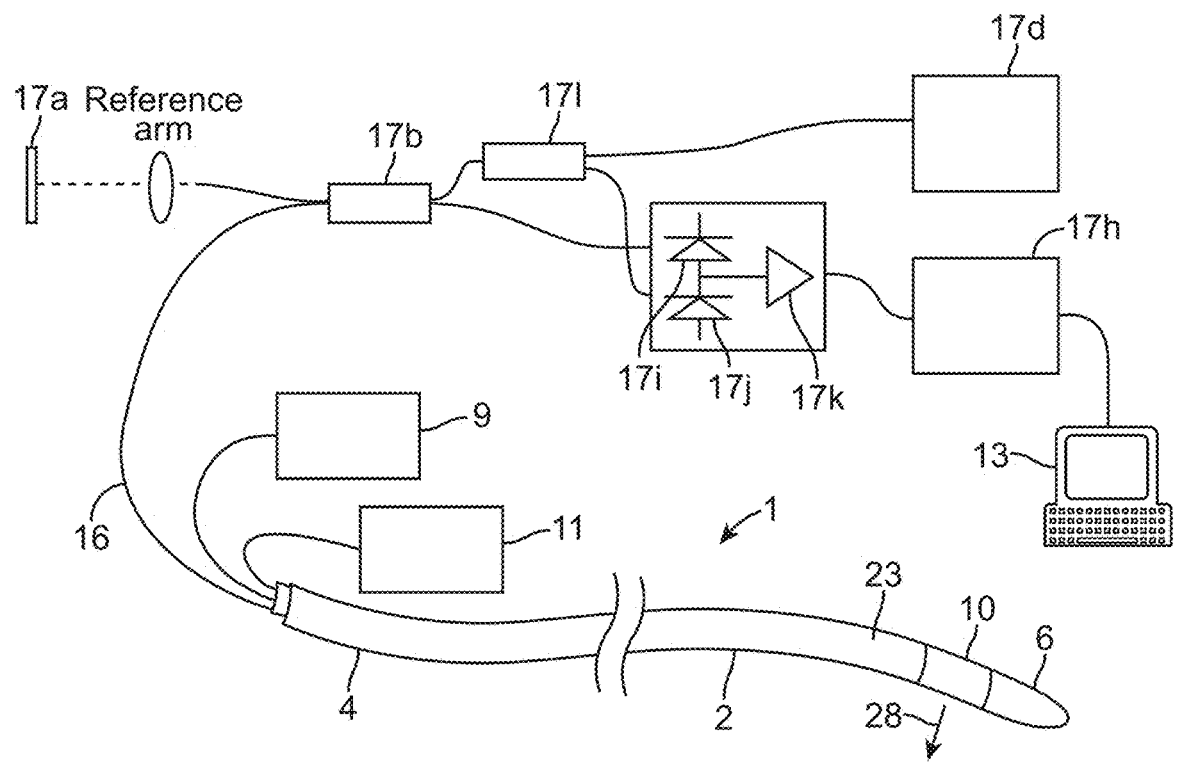
FIG. 1B illustrates an imaging probe in accordance with other embodiments.
Figure 1C:
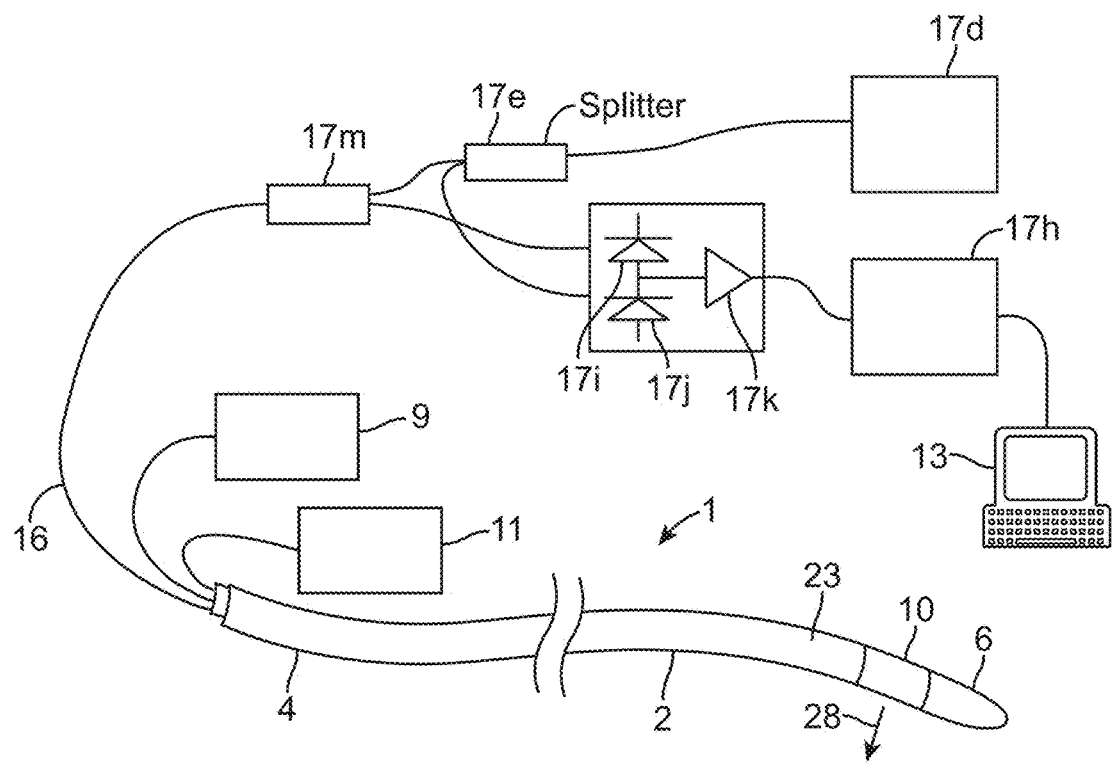
FIG. 1C illustrates an imaging probe in accordance with other embodiments.

It should be noted that the imaging system is not limited to the example described previously, and that in other embodiments, the imaging system may have other configurations. FIG. 1B illustrates another imaging system, which is similar to that shown in FIG. 1A, except that the coupler 17b and circulator 17l are used to form a Michelson interferometer, similarly having reference and sample arms whereby reference arm is optically communicated to the mirror 17a, and sample arm is optically communicated to the imaging probe 1. FIG. 1C illustrates another imaging system, which is similar to that shown in FIG. 1A, except that it includes a circulator 17m optically communicated to the imaging probe 1 to form a common path interferometer, whereby both reference and sample arm optical beam paths are combined, and where the reference mirror 17a is now present within the optical beam path within the imaging probe 1.

Figure 2:
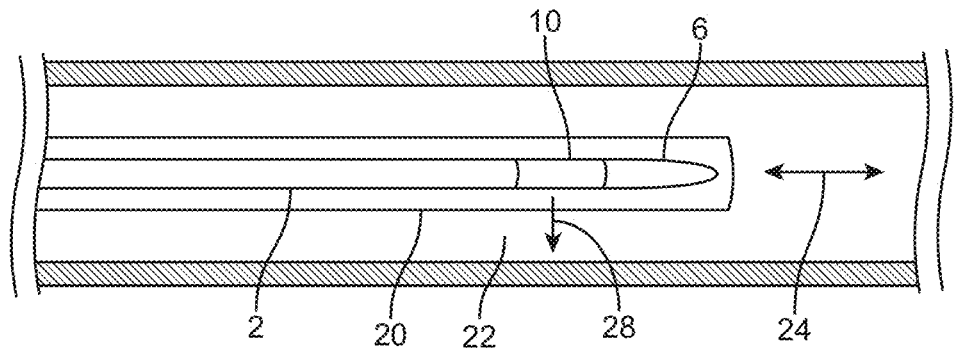
FIG. 2 illustrates an imaging probe that includes a sheath in accordance with some embodiments.

As shown in FIG. 2, in some embodiments, the imaging probe 1 of FIG. 1 may be placed within an elongated sheath 20. In some embodiments, part of the sheath 20 along its length may have a transparent region (similar to region 10 on the probe 1) so that light from the imaging probe 1 may exit through the transparent region of the sheath 20. In such cases, the length of the transparent region at the sheath 20 may be longer than the transparent region 10 at the imaging probe 1, so that when the probe 1 is placed at different positions relative to the sheath 20, light from the probe 1 can exit through the transparent region at the sheath 20. In other embodiments, the entire sheath 20 may be transparent. During use, the imaging probe 1 within the elongated sheath 20 can be placed in a narrow void or lumen 22 inside a patient to perform imaging using the focused light beam 28. The imaging probe 1 can be moved along the inside of the elongated sheath 20 (shown by arrow 24) to allow for imaging of the narrow void or lumen 22 along a preferred region. The sheath 20 is advantageous in that it prevents the probe 1 from rubbing against tissue during use. In other embodiments, the sheath 20 may not have any transparent region. In such cases, after the sheath 20 is desirably placed within the lumen 22 inside the body, the probe 1 can be deployed out of an opening at a distal end of the sheath 20.

Figure 3:
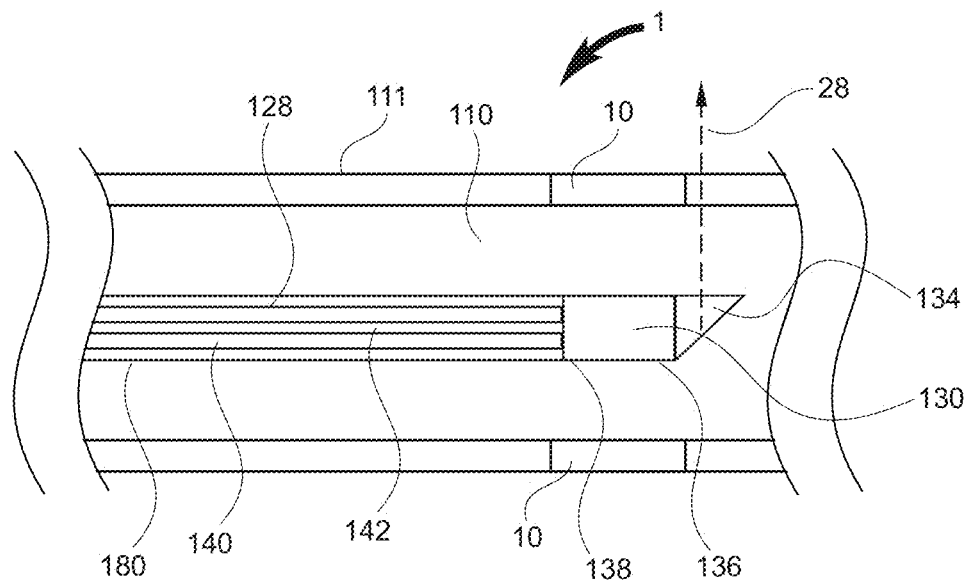
FIG. 3 illustrates some components at a distal end of an imaging probe in accordance with some embodiments.

As discussed, the imaging probe 1 allows the light beam 28 to exit through the region 10 at different angles. Such may be accomplished by turning an optical waveguide (e.g., an optical fiber) and a beam director located inside the imaging probe 1. FIG. 3 illustrates a distal end of the imaging probe 1 that includes an optical system 110 located within the imaging probe 1 in accordance with some embodiments. In some embodiments, the imaging probe 1 may be a flexible catheter. In other embodiments, the imaging probe 1 may be rigid. The optical system 110 includes an optical waveguide 128, a grin lens 130, and a beam director 134. As shown in the figure, the optical waveguide 128 may be an optical fiber having a core 142 and a clad layer 140. The optical waveguide 128 may also optionally further include material, e.g., one or more polymeric layer(s)/coating(s), surrounding the clad layer 140. The optical fiber core 142 is configured to provide a light beam 28, which is then optically processed (e.g., transmitted, shaped (such as collimated, focused, or both), etc.) by the grin lens 130, and the beam director 134. The processed light beam 28 then exits through the transparent region 10 of the imaging probe 1. In other embodiments, instead of an optical fiber, the optical waveguide 128 may include a hollow reflective capillary tube, a capillary tube with an inside diameter coated with at least one dielectric coating, a photonic crystalline fiber (also known as a Holley fiber), or any optical transmitter that is capable of transmitting light. The optical waveguide 128 aligns with the grin lens 130, which collimates the diverging light from the waveguide 128.

The grin lens (or gradient index lens) 130, is a special lens that has the ability to shape light directed through it. In some embodiments, the grin lens 130 may be cylindrical in shape, having flat perpendicular ends, or having slanted faces around 8 degrees to decrease back reflections into other optical systems. In some embodiments, the grin lens 130 shapes the light through it by having a gradient index profile across the radius of the lens. This refractive index profile may be parabolic in shape. The gradient index constant, g, determines how "strong" the grin lens 130 will focus light. The grin lens 130 may be used to focus, or collimate, or both collimate and focus light passing through it. The grin lens 130 differs from a standard convex lens in that the standard convex lens has a curvature shape which shapes the light passing through it, and the lens itself has a constant refractive index profile across the lens.

A grin lens may be made from glass and may have a varying refractive index profile achieved by either layering different types of glasses with different index profiles such as using a chemical vapor deposition technique. Another way to make a glass grin lens is to have a preform of cylindrical glass by doping or by boron diffusion. Through the diffusion, and diffusion gradient, a varying refractive index profile may be achieved. Another way to make a glass grin lens is by ion exchange with liquid lithium, where diffusion of sodium or lithium form a gradient through the glass material, resulting in a gradient index profile. In another method of making a glass gradient index lens, a preformed glass maybe ion stuffed by filling the glass pores with different types of salts, to create a diffusion gradient of the different salts, thereby resulting in a gradient index profile.

In some embodiments, the glass preform maybe ground to form their final shape and size, or maybe drawn in a fiber melting tower as to draw the preform into an optical fiber, where the optical fiber has a gradient index constant. This optical fiber may then be trimmed to the appropriate length to create a lens with the desired focusing and/or collimation properties.

While glass grin lenses may give desirable optical properties, manufacture and cost may prohibit them for being used in applications requiring large volumes of production or low cost. Thus, in accordance with some embodiments, the grin lens 130 may be formed using polymer. Polymer gradient index lenses are highly advantageous in that they may be made in large volumes at lower cost. In one way to create a polymer gradient index lens, a plastic polymer preform (with a varying gradient index profile achieved by doping, ion exchange, or ion stuffing, or layering different refractive index profiles across the radius of the preform) may create a gradient index constant. This preform may then be ground and cut to create the final shape and size of the grin lens, or maybe drawn in a fiber melting tower as to draw the preform into an optical fiber, where the optical fiber has a gradient index constant. This optical fiber may then be trimmed to the appropriate length to create a lens with the desired focusing and/or collimation properties.

Alternatively the gradient index lens 130 may be created using two different polymer liquids having different refractive indices. These liquid polymers are placed within a form, and are then spun to distribute the polymers. This results in the polymers mixing, and thus creating a gradient index profile. UV curing, radiation curing, or heat curing the polymer material may result in a solid grin lens.

In another method to create a polymer grin lens, two polymer materials that are solid, and have different refractive index profiles, maybe melted together to form a gradient index profile across its radius.

In another method to create a polymer grin lens, two polymers of different refractive index profiles are co-extruded together, the co-extrusion of the melted polymer materials creating a mixed distribution of the two polymer materials, forming a gradient index profile across the profile of the extrusion. The extrusion die may be sized such that a desired outer diameter of the grin lens may be achieved. Further creating a smaller diameter may be achieved by heating and drawing the extrusion. The extrusion is a long polymer fiber which may then be trimmed to the appropriate length to create a grin lens of the desired focusing and/or collimation properties.

In some embodiments, the grin lens 130 may be made from an injection molding technique, a compression molding technique, or any of other known techniques for shaping polymeric substance into a desired shape.

As shown in FIG. 3, the component 110 may optionally further include a tube 180 surrounding the optical waveguide 128. The tube 180 (or the tube 180 together with the optical waveguide 128) may function as a rotating tubular shaft during use. In other embodiments, the tube 180 is not included, and the optical waveguide 128 may function as a rotating shaft during use.

During use, the component 110 is configured to rotate within the probe 1 at a high rotation rate. In some embodiments, the component 110 may turn at 2000 rpm or higher, and more preferably at 10000 rpm or higher. For example, in some embodiments, the component 110 may rotate at a rate that is anywhere from 10000 to 50000 rpm. In further embodiments, the component 110 may rotate at a rate that is higher than 50000 rpm.

Figure 3A:
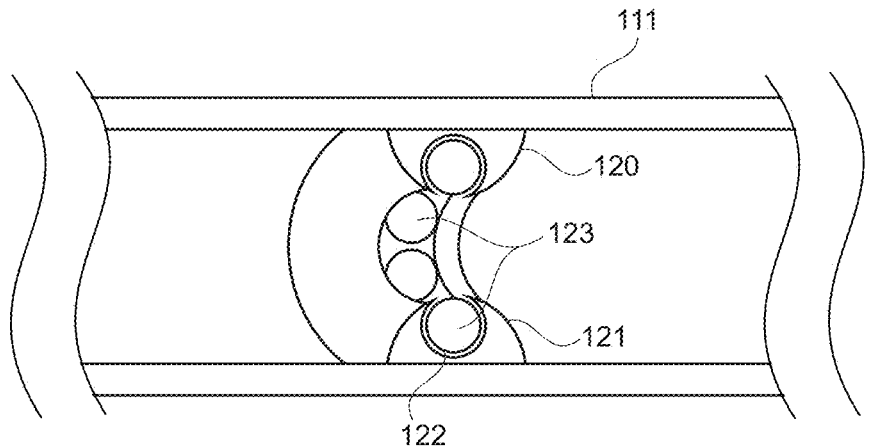
FIG. 3A illustrates a bearing component in accordance with some embodiments.

In one or more embodiments, the component 110 may be rotationally supported in the probe 1 using bearings or sheath 111. In some embodiments, the bearings may be ceramic bearings for reducing dust and for allowing the component 110 to rotate at a fast rate. FIG. 3A illustrates a bearing component 120 in accordance with some embodiments. The bearing component 120 includes a housing 121 having a groove 122 that partially houses a plurality of ceramic bearings 123. The housing 121 has a ring shape that corresponds with a cross sectional shape of the sheath 111 so that the housing 121 may be secured to an interior surface of the sheath 111. The bearings 123 are rotatable within the groove 122 of the housing 121, thereby providing rotational bearing support for the component 110 and/or tube 180 relative to the sheath 111. In some embodiments, the sheath 111 may include a plurality of the bearing components 120 disposed at different locations along the length of the sheath 111.

In other embodiments, other types of bearings may be used. Also, in further embodiments, the interior surface of the sheath 111 itself may be used as a bearing for rotatably supporting the component 110.

Also, in the illustrated embodiments, the grin lens 130 is aligned with the beam director 134. The grin lens 130 may include a distal end 136 for securing to the beam director 134, and a proximal end 138 for securing to the optical waveguide 128. The beam director 134 may be an optical component that is capable of changing a path of a light. For example, the beam director 134 may be a mirror, or a prism.

The beam director 134 is configured to direct (e.g., deflects) the light so that the light changes direction. In the illustrated embodiments, the light leaving the beam director 134 travels in a direction that is 90° from the original path of the light. In other embodiments, the light leaving the beam director 134 may travel in a direction that forms other angles relative to the original path. As shown in the figure, the beam director 134 is next to the transparent region 10 at a position along a longitudinal axis of the imaging probe 1. This allows light leaving the beam director 134 to exit through the transparent region 10. As shown in the figure, the optical waveguide 128, the grin lens 130, and the beam director 134 are configured to rotate about the axis of the waveguide 128, so that the light beam 28 may exit through the region 10 at different angular positions. In some embodiments, the optical system 11 may optionally further include a focusing lens (not shown). The focusing lens may be disposed between the beam director 134 and the region 10, and may be coupled to the beam director 134. The light beam 28 is directed by the beam director 134 radially from the longitudinal axis of optical waveguide 128, and is optically communicated to the focusing lens, which focuses the light beam 28 to form an output light.

The output light provided by the probe 1 impinges on tissue, and is reflected back towards the imaging probe 1. The reflected light enters through the transparent region 10, and is transmitted by the focusing lens (if one is included). The light is then directed by the beam director 134 towards the grin lens 130. The grin lens 130 then couples into optical waveguide 128. The optical waveguide 128 transmits the light to components 3 and 7 (see FIG. 1) for processing the light signal. Thus, as illustrated in the above embodiments, the grin lens 130 has bi-directional properties (i.e., collimation in one direction, and light-focusing in the other direction), and the focusing lens also has bi-directional properties (i.e., light-focusing in one direction, and collimation in the other direction). Accordingly, as used in this specification, the term "grin lens" is not limited to an optical device that only performs collimation, and may refer to any optical device that is capable of performing other functions, such as, light focusing. Similarly, as used in this specification, the term "focusing lens" is not limited to an optical device that only performs light focusing, and may refer to any optical device that is capable of performing other functions, such as, light collimation. Also, in any of the embodiments described herein, any of the optical components may have uni-directional property or bi-directional properties.

In further embodiments, instead of having the focusing lens at the downstream side of the beam director 134, the focusing lens may be placed upstream to the beam director 134. In such cases, the grin lens 30 is configured to change a diverging light 28 to have a collimated beam. The collimated beam 28 reaches the focusing lens and is focused by the focusing lens before the light is processed by the beam director 134.

Also, in any of the embodiments of the imaging probe 1 described herein, the grin lens 130 may be implemented using micro optic(s), fiber lens, other any of other known devices, to process the beam. As discussed herein, the grin lens 130 may be located in the axis that is coincident with the axis of the transmitted light provided by the optical waveguide 26. Also, in any of the embodiments of the imaging probe 1 described herein, the focusing optics may be located in line with the grin lens 130, or may be located 90 degrees (or at other angles relative) to the emitted light axis from the optical waveguide 128. Furthermore, in any of the embodiments of the imaging probe 1 described herein, the beam director 134 may include a concave mirror, which not only direct the light beam at a certain angle (e.g., 90°), but also to focus it as well. In still further embodiments, any of the embodiments of the imaging probe 1 may include optical device(s) that function as filter(s), such as notch, shortpass, longpass, bandpass, fiber Bragg gratings, optical gratings. Such optical device(s) may be placed in line with the optics described herein to further provide optical manipulation of the light as it is emitted or detected by the probe 1 for optical enhancement. In any of the embodiments of the imaging probe 1 described herein, the optical components in the probe 1 may be configured (e.g., positioned, placed, arranged, etc.) to allow bidirectional coupling of light to and from the proximal and distal ends of the probe 1.

As discussed, in some embodiments, the optical waveguide 128 may be an optical fiber. In some embodiments; the optical fiber may be a singlemode fiber having a core diameter of 4.3 microns, 9.2 microns, or generally a 3-10 micron core size depending on the wavelength and actual mode field diameter. The cladding layer of the single mode fiber may be 80 microns or 125 microns with a coating layer between 125 microns to 300 microns, and more preferably anywhere from 135 to 250 microns. In other embodiments, the optical fiber may be multimode fibers. Multimode fibers may a core diameter ranging between 20-100 microns, such as 50 microns, 62.5 microns, 100 microns, etc. The clad layer for the multimode fibers may be 100-500 microns, such as 250 microns in diameter. Multimode fibers may be advantageous because they have a larger core diameter and thus are less susceptible to dust and dirt contamination, or optical misalignment in the optical system relative to the optical sensor or optical interrogator system that may cause optical signal degradations. In further embodiments, a photonic crystalline fiber (PCF) may be used for the optical waveguide 128. Photonic crystalline fiber exhibits unique properties such as being endlessly single mode across a wide spectral range, such as from 200 to 2000 nanometers. In still further embodiments, fiber bundles having multiple fibers bundled together may be used for the optical waveguide 128. Thus, as used in this specification, the term "optical fiber" or similar terms, such as "fiber" may include one or more fibers. Furthermore, in other embodiments, the waveguide 128 may include double clad, triple clad, quadruple, or "many" clad fibers.

Figure 4:
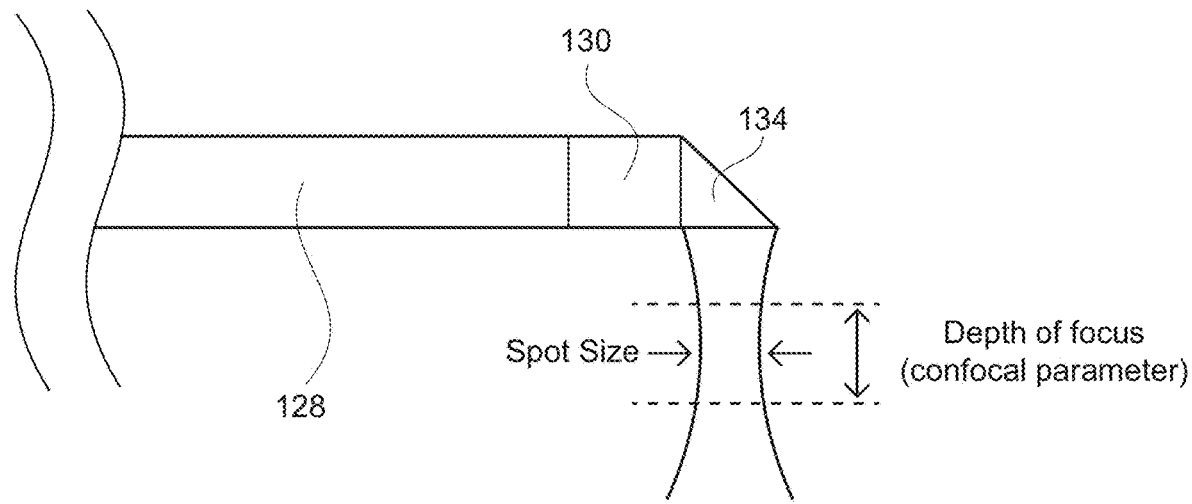
FIG. 4 illustrates a depth of focus and a spot size provided by a beam director in accordance with some embodiments.

As shown in FIG. 4, the grin lens 130 and the beam director 134 of the imaging probe 1 are configured to direct the optical beam from the optical waveguide 128 and to focus and direct the optical beam so that the beam has a depth of focus with a spot size. In some embodiments, the beam may be used to radially image a vessel or lumen inside a patient. In some embodiments, the imaging optics may provide 100 um of spot size at the beam waist or less. Also, in some embodiments, the spot size may be anywhere from 0.5 microns to 500 microns, and more preferably anywhere from 0.5 microns to 100 microns, and even more preferably anywhere from 0.5 microns to 50 micron, such as 20-40 microns. A smaller spot size allows the imaging probe 1 to have higher optical resolution in imaging. In other embodiments, the spot size may have values that are different from the above example. Also, the imaging optics may provide a depth of field of at least 30 microns, and more preferably at least 100 um, and even more preferably anywhere from 500 um to 2000 um, and even more preferably 2000 um or higher, such as 3000-50000 um. In addition, in some embodiments, the imaging optics may provide a working distance of at least 100 um, and more preferably 500 um to 2000 um, and even more preferably anywhere from 500 um to 50000 um. In some embodiments, the working distance is within an imaging range of the minimal and maximal diameters of the lumen to be imaged. For example, in some embodiments, the lumens in a patient to be imaged may be anywhere from 100 um to 50000 um in diameter. In such cases, the working distance of the imaging probe 1 may be configured to provide such imaging range. In other cases, where the imaging probe 1 may be off center within the lumen to be imaged, requiring the imaging range to be greater as to fully image the lumen. In some embodiments, the grin lens 130 is configured to both collimate and focus the optical beam to a desired working distance, depth of field, and imaging spot size resolution.

Figure 5:
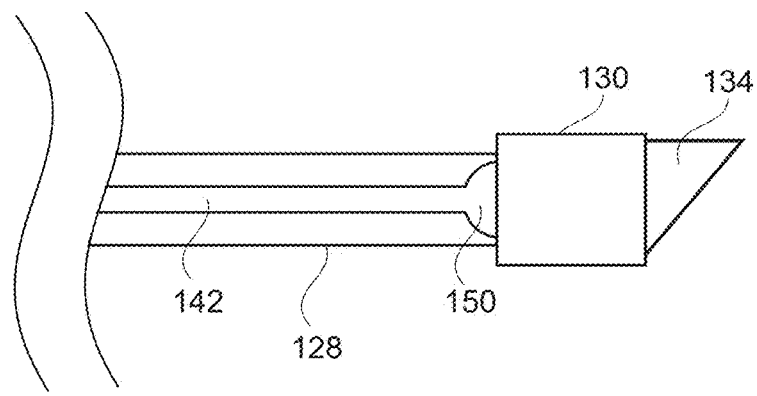
FIG. 5 illustrates some components at a distal end of an imaging probe in accordance with some embodiments.

In one or more embodiments, a highly diverging beam, or larger beam diameter may be created by thermally expanding the distal end 150 of the optical fiber core 142 in the waveguide 128 (FIG. 5). Thermally expanding the core of waveguide 128 increases the beam entry diameter into the grin lens 130 as to enable the grin lens 130 to have a longer or shorter working distance, longer or shorter depth of focus, and/or larger or small beam waist spot size. This thermally expanded core 142 may be achieved by heating the distal end 150 of an optical fiber core 142 by using a gas flame, plasma beating, electron beam heating, laser heating, or any of other techniques of apply large thermal energy to the end of the optical fiber core 142 as to cause the optical fiber core to expand. In one example the core diameter of a single mode SMF 28 fiber may be approximately 9 um, and the distal end of such fiber may be expanded to have a diameter of 20 um, or larger (e.g., 100 um).

Figure 6:
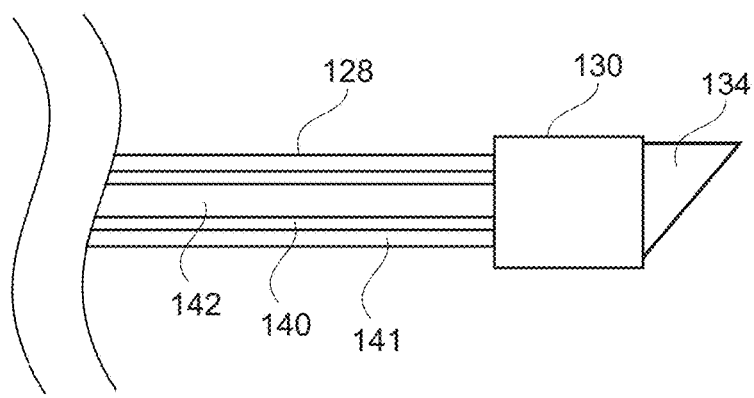
FIG. 6 illustrates some components at a distal end of an imaging probe in accordance with some embodiments.

In one or more embodiments, the optical waveguide 128 further includes a polymeric coating 141 (FIG. 6). The polymeric coating 141 surrounds the clad layer 140 and the optical fiber core 142. When attaching the optical waveguide 128 to the grin lens 130, the optical fiber core 142 with the polymeric coating 141 is directly coupled to the grin lens 130.

Figure 7:
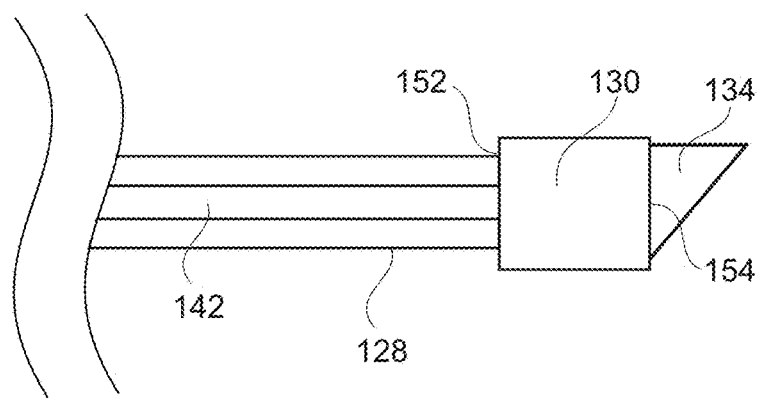
FIG. 7 illustrates an optical fiber coupled to a grin lens using an adhesive in accordance with some embodiments.

Various techniques may be employed to secure the grin lens 130 relative to the optical waveguide 128. In some embodiments, the optical fiber core 142 may be attached to the grin lens 130 using an adhesive 152 (FIG. 7). In some cases, the fiber core 142 and the clad together may be attached to the grin lens 130. The beam director 134 may also be attached to the grin lens 130 using an adhesive 154. In some embodiments, the adhesive 152 and/or 154 may be an optical adhesive, such as a UV curable adhesive. The adhesive may match the refractive index of the optical fiber core 142 in the waveguide 128 and the grin lens 130 to reduce optical back reflections through the imaging system and optical fiber core 142 that would degrade image quality. In some cases, the refractive index mismatch between the grin lens 130 and the optical fiber core 142, or the between grin lens 130 and the beam director 134, forms a partially reflective interface having a reflectance value of 0.001 percent to 10 percent, more preferably 0.1 percent to 5 percent, and even more preferably 0.3 percent to 0.8 percent. This allows a reflective reference surface for imaging calibration to be formed, which in turn provides a common path interferometer within imaging probe 1. The refractive index of adhesive 152 and 154 maybe anywhere from 1.3 to 2.2, and more preferably anywhere from 1.4 to 1.7, and even more preferably anywhere from 1.5 to 1.6.

In other embodiments, the grin lens 130 may be attached to the optical waveguide 128 by fusion splicing, where fusion splicing is achieved by thermally bonding or melting the optical fiber core 142 and grin lens 130 together. This process may melt the fiber core 142 and clad together to the grin lens 130. In such cases, the melted portion of the fiber core 142 and the grin lens 130 effectively form the adhesive 152. This may be achieved by a commercially available fusion splicer that uses an electrical arc, laser beam, or heating element as the heat source for melting the optical fiber core 142 and grin lens 130 together to form a mechanical attachment.

In other embodiments, the grin lens 130 may be attached to the optical waveguide 128 or the beam director 134 by means of solvent bonding if any of the components of the optical waveguide 128, the beam director 134, or the grin lens 130 are made from a polymeric material, such as polycarnonate, acrylic, cyclic olefin copolymer, or other optically transmissive polymer. Solvents used to bond the optical waveguide 128, beam director 134, or grin lens 130 maybe methylene chloride, acetone, or xylene.

Figure 8:
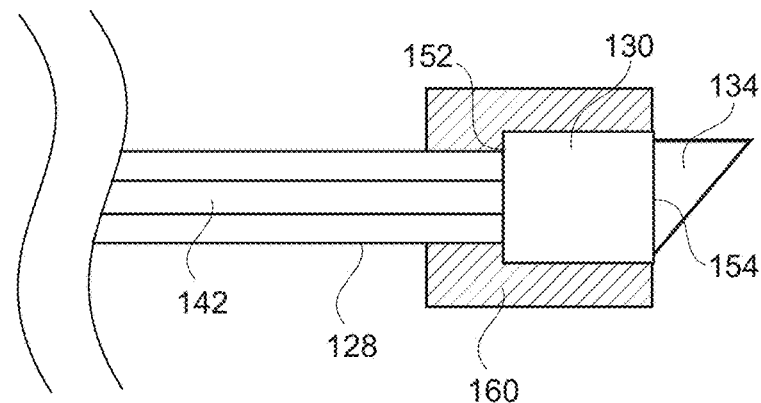
FIG. 8 illustrates an optical fiber coupled to a grin lens using a ferrule in accordance with some embodiments.

In some embodiments, while the optical waveguide 128 may be attached to the grin lens 130 using an adhesive, a ferrule 160 may optionally be provided to align the optical waveguide 128 and the grin lens 130, and/or to held the optical waveguide 128 fixed in position relative to the grin lens 130 (FIG. 8).

Figure 9:
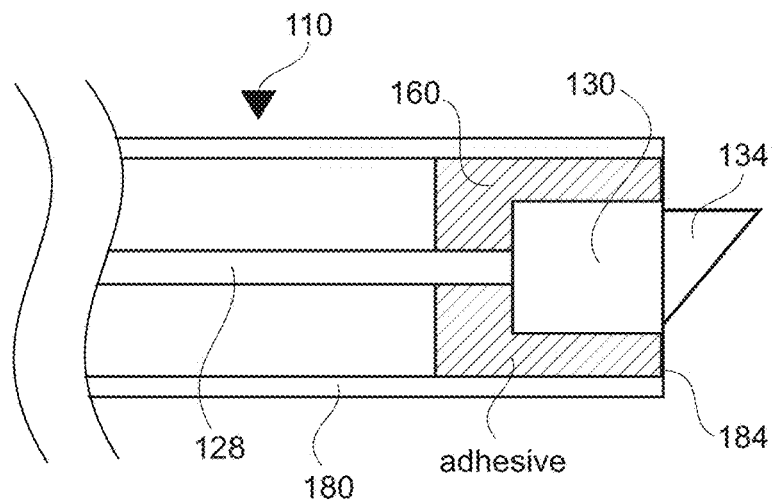
FIG. 9 illustrates an optical fiber coupled to a grin lens using a ferrule in accordance with other embodiments.
Figure 10:
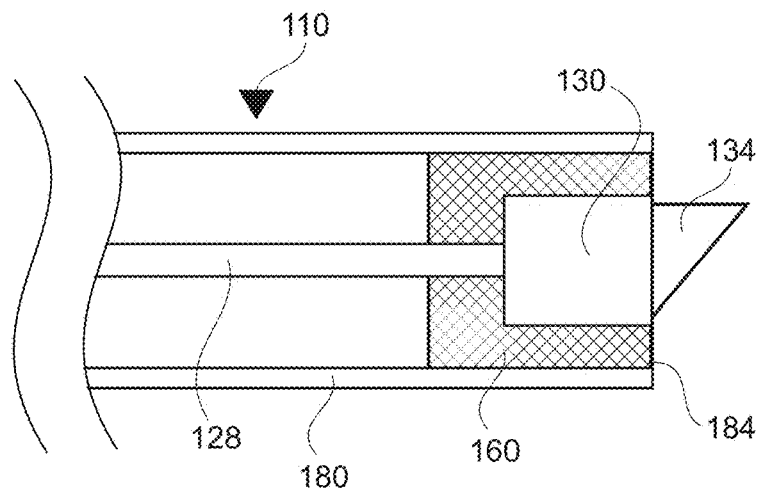
FIG. 10 illustrates an optical fiber coupled to a grin lens using a ferrule in accordance with other embodiments.

In some embodiments, the optical waveguide 128 may be attached to the grin lens 130 using an adhesive, and the beam director 134 may be attached to the grin lens 130 using an adhesive. In such cases, the component 110 may include the tube/shaft 180 and a ferrule 160 located inside the tube 180 at the distal end of the tube 180 (FIG. 9). The optical waveguide 128 and the grin lens 130 are located within the ferrule 160 as to align and mechanically hold the optical waveguide 128 and grin lens 130 relative to each other. In some embodiments, the ferrule 160 may be formed by an adhesive and the entire assembly is located within the tube 180. The grin lens 130 may be flush with the end 184 of the tube 180. During use the tube 180 functions as a rotating shaft that contains the optical waveguide 128. In other embodiments, instead of forming the ferrule 160 using an adhesive, the ferrule 160 may be formed first, and is then assembled together with the grin lens 130 (FIG. 10). For examples, the ferrule 160 may be formed as a machined component, or may be molded.

Figure 11:
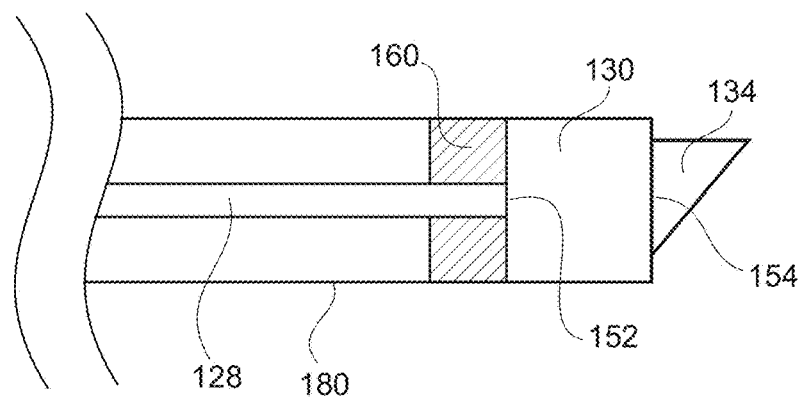
FIG. 11 illustrates a distal end of an imaging probe that includes a ferrule in accordance with some embodiments.
Figure 12:
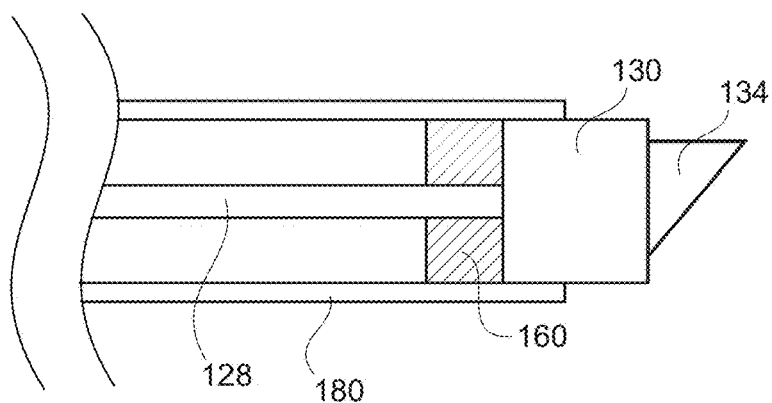
FIG. 12 illustrates a distal end of an imaging probe that includes a ferrule in accordance with other embodiments.
Figure 13:
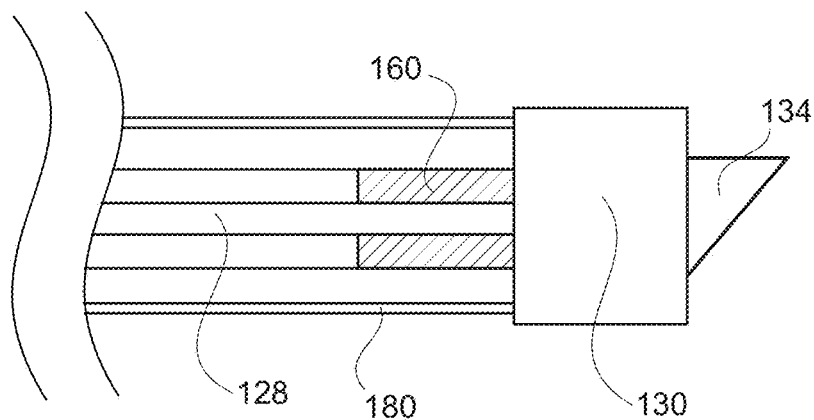
FIG. 13 illustrates a distal end of an imaging probe that includes a ferrule in accordance with other embodiments.

In other embodiments, the optical waveguide 128 may be fixed in place relative to the tube 180 using a ferrule 160, and the grin lens 130 may be secured to the distal end of the tube 180 (FIG. 11). The ferrule 160 may be formed using an adhesive. Alternatively, the ferrule 160 may be formed separately (e.g., as a molded or machined part), and the ferrule 160 is then assembled to the optical waveguide 128 and the tube 180. The ferrule 160 aligns the optical waveguide 128 relative to the tube 180 and to the grin lens 130. In other embodiments, part or all of the grin lens 130 may extend out of the distal end of the tube 180 (FIG. 12). In some embodiments, if the entire grin lens 130 is outside the distal end of the tube 180, the grin lens 130 may have a surface that is flush with the exterior surface of the tube 180 (FIG. 13). Alternatively, the grin lens 130 may have a cross sectional dimension that is larger than the cross sectional dimension of the tube 180. The optical waveguide 128 may be attached to the grin lens 130 using an adhesive 152, and the beam director 134 may be attached to the grin lens 130 using an adhesive 154.

Figure 14:
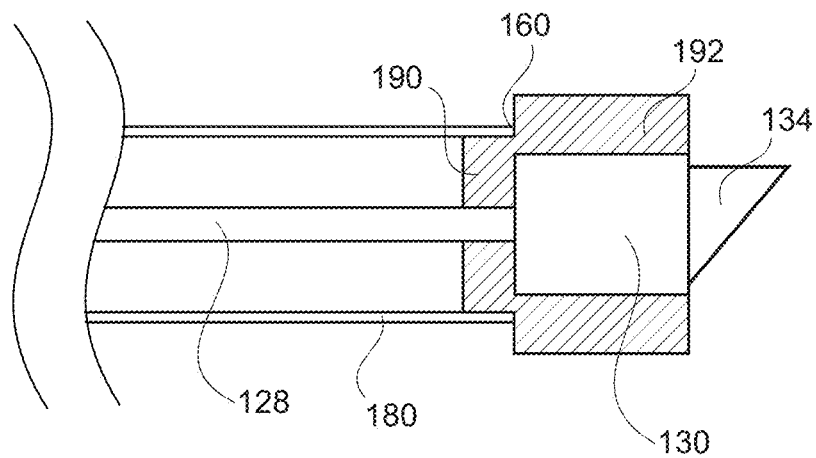
FIG. 14 illustrates a distal end of an imaging probe that includes a ferrule in accordance with other embodiments.

Also, in some embodiments, the ferrule 160 for coupling to the optical waveguide 128 and the grin lens 130 may extend out of the distal end of the tube 180 (FIG. 14). As shown in the figure, the ferrule 160 has a first portion 190 that is housed within the distal end of the tube 180, and a second portion 192 that extends out of the distal end of the tube 180. In the illustrated embodiments, the second portion 192 of the ferrule 160 has a cross sectional dimension that is larger than a cross sectional dimension of the tube 180. In other embodiments, the cross sectional dimension of the second portion 192 may be the same as, or may be less than, the cross sectional dimension of the tube 180.

Figure 15:
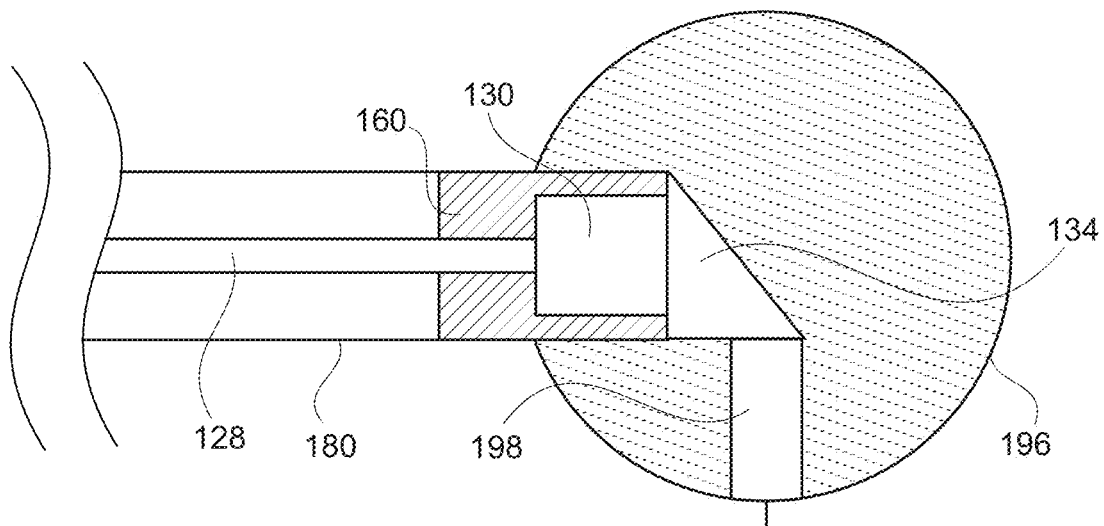
FIG. 15 illustrates a distal end of an imaging probe that includes a housing containing a beam director in accordance with some embodiments.

In other embodiments, at least a part of the ferrule 160 may be a spherical housing 196 that houses the beam director 134 (FIG. 15). The spherical housing 196 may have an optical port 198 for allowing light to be transmitted therethrough to and from the beam director 134. Alternatively, the spherical housing 196 may be made from an optically transparent material, in which cases, the port 198 is not needed. In the illustrated embodiments, the proximal portion of the ferrule 160 aligns and secures the optical waveguide 128 and the grin lens 130 relative to each other, while the distal portion of the ferrule 160 with the spherical housing 196 aligns and secures the grin lens 130 relative to the beam director 134. In other embodiments, the distal portion of the ferrule 160 may have a shape that is different from a spherical shape. For example, the distal portion of the ferrule 160 may have a square shape, a rectangular shape, an elliptical shape, or a customized shape.

Figure 16:
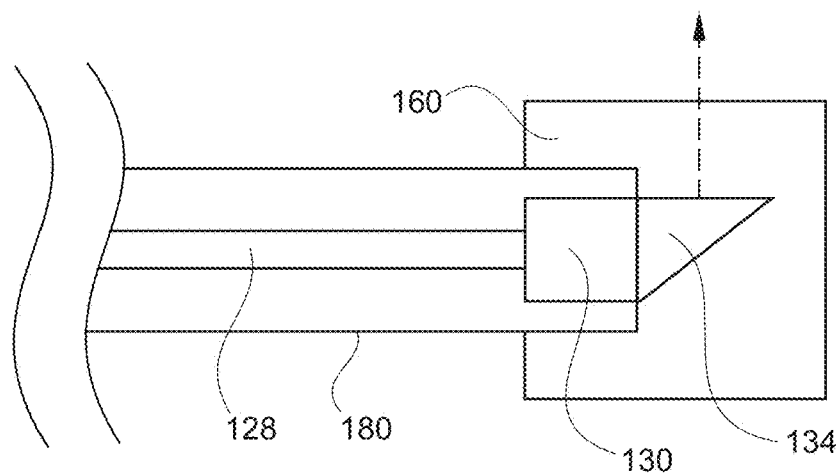
FIG. 16 illustrates a distal end of an imaging probe that includes a housing containing a beam director in accordance with other embodiments.

In other embodiments, the ferrule 160 may encapsulate the entire grin lens 130 and the beam director 134 (FIG. 16). In such cases, all or part of the ferrule 160 may be made from an optically transparent material so that light can be transmitted therethrough to and from the beam director 134. Alternatively, the ferrule 160 may be made from a non-optically transparent material, in which case, the ferrule 160 may include a port (not shown) that is aligned with the beam director 134 so that light may be transmitted through the slot to and from the beam director 134. In the illustrated embodiments, the grin lens 130 is located completely within the tube 180. In other embodiments, the grin lens 130 may be partially extended out of the distal end of the tube 180, or may be completely outside the distal end of the tube 180. In the illustrated embodiments, the ferrule 160 has a rectangular shape. In other embodiments, the ferrule 160 may have a shape that is different from a rectangular shape. For example, the ferrule 160 may have a square shape, a spherical shape, an elliptical shape, or a customized shape.

It should be noted that any of the examples of the attachment methods described herein may also be used to secure other optics or fiber spacers (if they are present) in the imaging probe 1 to achieve the required imaging specifications (e.g., working distance, depth of focus, and spot size diameter resolution).

In any of the embodiments described herein, the tube 180 containing the optical waveguide 128 may have a cross sectional dimension that is less than 1000 um, and more preferably less than 1000 um, and even more preferably less than 80000 um (e.g., 400 um, or less). In other embodiments, the tube 180 may have other cross sectional dimensions. For example, in other embodiments, the tube 180 may have a cross sectional dimension that is larger than 1000 um, such as 1000-10000 um.

Figure 17:
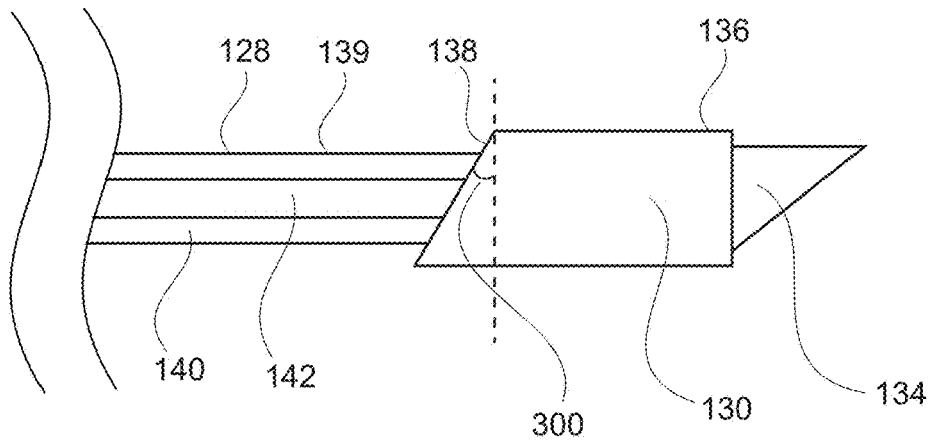
FIG. 17 illustrates a slanted interface between a grin lens and an optical fiber in accordance with some embodiments.

As shown in FIG. 17, in one or more embodiments (e.g., in any of the embodiments of FIGS. 3-16), the proximal end 138 of the grin lens 130 may have a slanted configuration with an angle 300 for mating with the distal end 139 of the optical waveguide 128. The distal end 139 of the optical waveguide 128 also has a slanted configuration for mating with the slanted proximal end 138 of the grin lens 130. The grin lens 130 may be secured to the optical waveguide 128 using any of the techniques described herein. The distal end 139 of the optical fiber 128 may also be cleaved and polished to reduce (or eliminate) back reflections. In some embodiments, the angle 300 for cleaving and polishing may be 8 degrees. In other embodiments, the angle 300 may be any value from 1 to 20 degrees. Also, in further embodiments, the angle 300 may be any value that is larger than 6.5 degrees.

Figure 18:
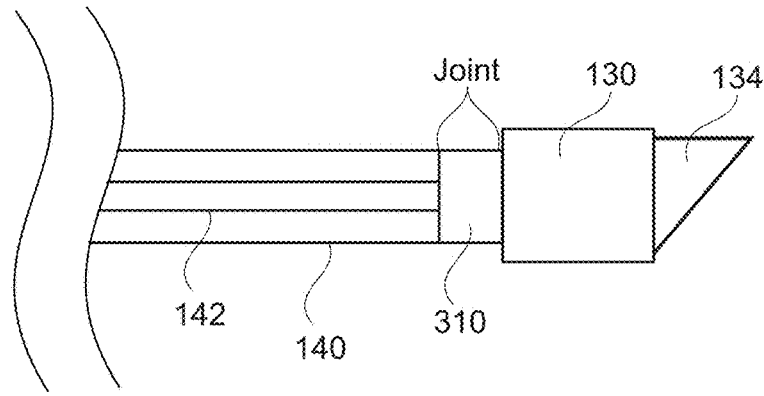
FIG. 18 illustrates a spacer disposed between a grin lens and an optical fiber in accordance with some embodiments.

In one or more embodiments (e.g., in any of the embodiments of FIGS. 3-16), the imaging probe 1 may include a fiber spacer 310 disposed between the optical fiber core 142 and the grin lens 130 (FIG. 18). The fiber spacer 310 may be secured to the distal end of the optical fiber core 142 (e.g., using an adhesive, fusion splicing, or any of other techniques), and the grin lens 130 may be secured to the distal end of the spacer 310. The spacer 310 may allow a beam transmitted from the optical fiber core 142 to diverge (increase in diameter) before optical transmission into the grin lens 130, to thereby achieve a longer or shorter working distance, larger or smaller focus spot size, and/or longer or shorter depth of focus depending on the length of fiber spacer 310. In some embodiments, the spacer 310 may be a section with no core fiber, in which the no core fiber has the same refractive index profile across its radius, forming a cylindrical glass or polymer spacer. In other embodiments, the fiber spacer 310 maybe a glass spacer made from BK7 glass, Pyrex glass, borisilicate glass, silicon, or other optically transparent material. In other embodiments, the fiber spacer 310 may be made from a polymer material such as polymethyl methylacralayte, polycarbonate, Cyclic olefin co-polymer, or other optically transparent polymers.

Figure 19:
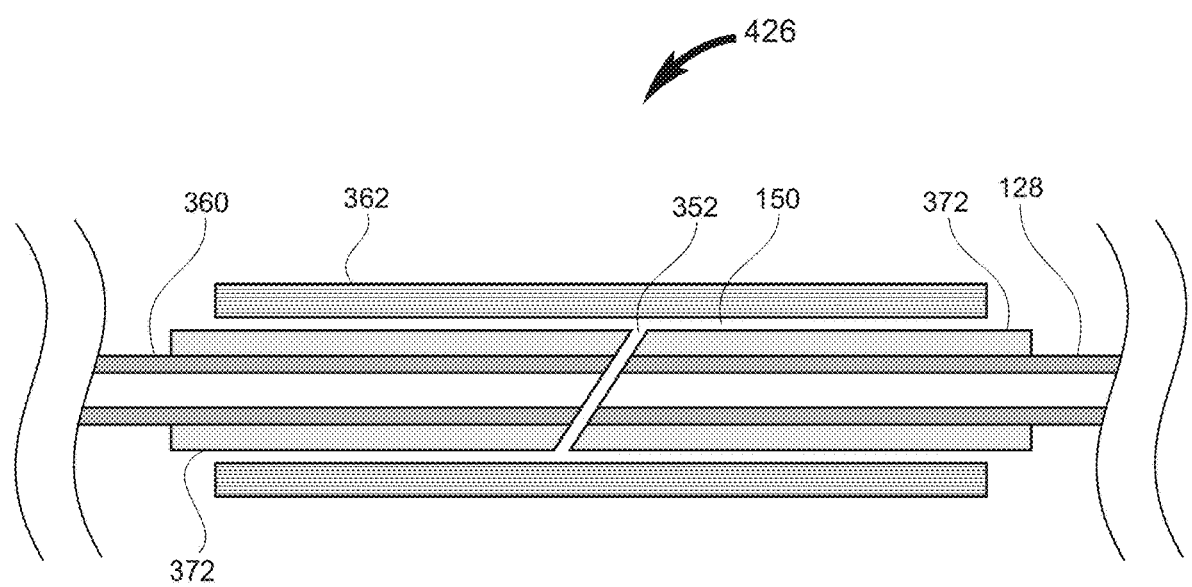
FIG. 19 illustrates a proximal end of the imaging device in accordance with some embodiments.

In some embodiments, the proximal end 150 of the optical waveguide 128 may also be terminated and polished (FIG. 19). As shown in the figure, the proximal end 150 of the optical waveguide 128 may have a slanted configuration with an angle 352, for mating with an optical waveguide 360 (e.g., an optical fiber). The optical waveguide 360 also has a slanted configuration for mating with the proximal end 150 of the optical fiber 128. The slanted configuration at the joint between the optical waveguide 128 and the waveguide 360 allows back reflections to be reduced (or eliminated). In some embodiments, the angle 352 may be 8 degrees. In other embodiments, the angle 352 may be any value from 1 to 20 degrees. Also, in further embodiments, the angle 352 may be any value that is larger than 6.5 degrees. As shown in the figure, the proximal end 150 of the optical fiber 128 is inserted into a ferrule 372, and the distal end of the waveguide 360 is inserted into another ferrule 372. The two ferrules 372 are inserted into the alignment ferrule 362. The optical waveguide 128 or 360 may be connected to a sample arm of an optical interferometer or optical coherence tomography system. In some embodiments, the optical waveguide 128 may be connected to an optical rotary joint where optical waveguide 128 rotates and is optically coupled to an optical coherence tomography system. The ferrules 372 may be made from a ceramic or metal material with a precision hole down the middle, where the optical waveguides 128 and 360 are placed and bonded into place with adhesive, solder, or epoxy. After the optical waveguides 128 and 360 is bonded within the respective ferrules 372, it may be cleaved and polished. The ends of the ferrules 372 may also be angled as to reduce back reflections.

Optical connectors that may be used at the proximal end 150 of the optical waveguide 128 include a FC connector, a SC connector, a MT-RJ connector, an E2000 connector, a LC connector, or any of other known connectors. Also, in other embodiments, the connector may include a ceramic ferrule with a fiber bonded within it and polished.

Figure 20:
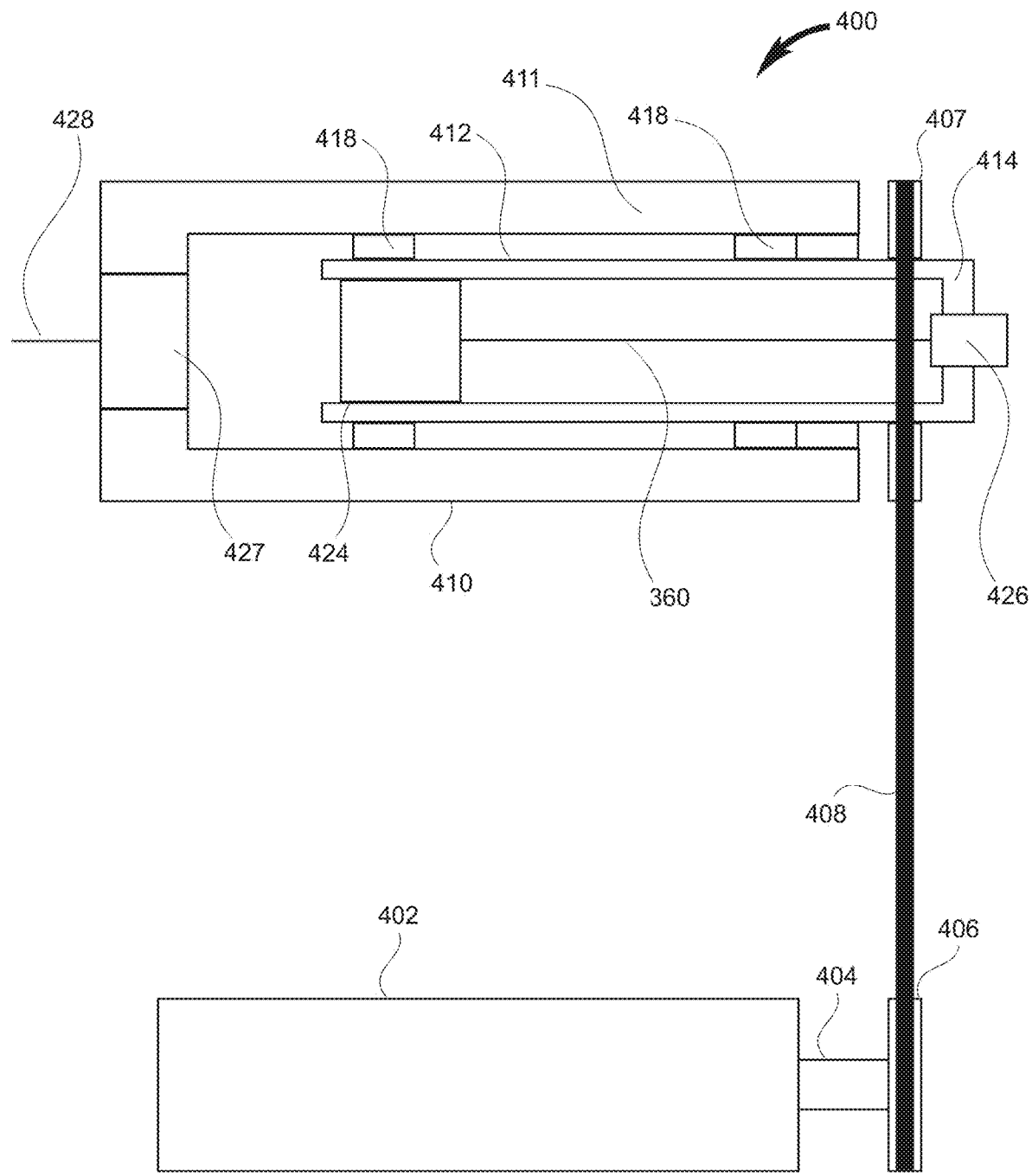
FIG. 20 illustrates a motor system for turning an optical fiber inside an image device in accordance with some embodiments.

As discussed, the optical waveguide 128 in the imaging probe 1 is configured to rotate during use. Various techniques may be employed to rotate the optical waveguide inside the imaging probe 1. FIG. 20 illustrates a motor system 400 for rotating an optical waveguide inside the imaging probe 1 in accordance with some embodiments. The motor system 400 includes a motor 402 (which may be an electric motor in some embodiments) for turning a motor shaft 404. In other embodiments, the motor 402 may be a stepper motor, brushless motor, coreless motor, or any device that is capable of providing a constant rotational motion. In some embodiments, the motor 402 may provide the rotary shaft 404 with a rotational speed of at least 1 rpm, 1000 rpm, or more preferably at least 3600 rpm, or even more preferably greater than 3600 rpm (such as 12000 rpm). In other embodiments, the motor 402 may rotate the shaft 404 at other rotational speeds. A pulley 406 is coupled to the motor shaft 404 so that rotation of the motor shaft 404 also turns the pulley 406. The motor system 400 also includes a drive belt 408 coupled to the pulley 406, which is coupled to pulley 407 and shaft 412 which then can turn fiber optic connector assembly 426. In other embodiments, the components 406 and 407 may be a gear system instead of a belt. As shown in the figure, the fiber optic rotary joint 410 includes a housing 411 that supports bearing 418 and rotably supports the shaft 412 therein. The drive belt 408 is coupled to pulley 407 a distal end 414 of the shaft 412, so that rotation of the pulley 406 will actuate the drive belt to rotate pulley 407 and the shaft 412 in the housing 411. The distal end 414 of the shaft 412 includes an optical waveguide connector 426 for coupling to the optical waveguide (e.g., the optical wave guide 128) in the probe 1. The optical waveguide connector 426 is coupled to an optical waveguide 360 (e.g., a fiber optic) located inside or shaft 412. During use, light is supplied to the optical waveguide 428, and is processed by the collimator 427. The light is then transmitted to the rotating collimator 424, which rotates together with the shaft 412 in response to actuation of the motor 402. The collimator 424 processes the light, and transmits it along the optical waveguide 360 to the optical waveguide connector 426. The optical waveguide connector 426 (which may include the alignment ferrule 362 (FIG. 19) holding ferrules 372 in place, in which the optical waveguides 128 and 360 are mounted) then transmits the light to the optical waveguide 128 in the probe 1. When the probe 1 received a reflected light through the region 10, the optical waveguide 128 transmits the reflected light back towards the fiber connector 426. The fiber connector 426 then transmits the light through the optical waveguide 360 towards the rotating collimator 424. The collimator 424 then passes the reflected light to the fixed collimator 427, which transmits the light signal through the optical waveguide 428. The optical waveguide 428 may be connected to the sample arm of an interferometer, to an optical coherence tomography system, or to other optical detection and processing system.

Figure 21:
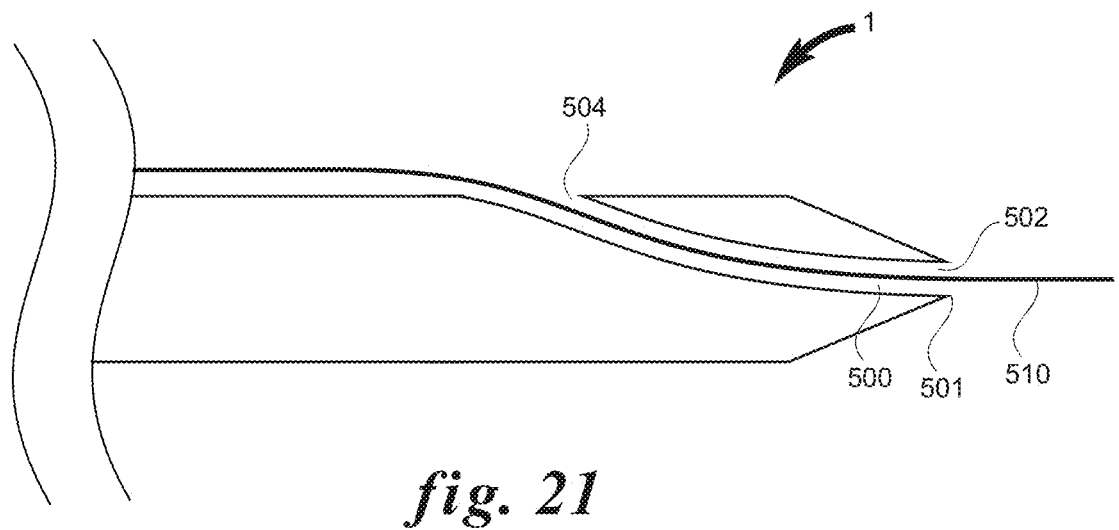
FIG. 21 illustrates an imaging device that includes a guidewire lumen in accordance with some embodiments.

In one or more embodiments, the imaging probe 1 may optionally further include a lumen for accommodating a guidewire to assist in placing the imaging probe 1 within a lumen located in a patient's body, particularly in lumens where the lumen path maybe tortious. For example, in some embodiments, the probe 1 may include a lumen 500 extending from an opening 501 at the distal tip 502 to an opening 504 along the length of the probe 1 (FIG. 21). During use a guidewire 510 may be inserted into the lumen 500 from the opening 501 at the distal tip 502 and may exit from the opening 504 (as in a monorail configuration). Alternatively, the guidewire 510 may enter from the opening 504 and may exit from the distal tip 502. In the illustrated embodiments, the guidewire 510 enters into the probe 1 at the center of the probe 1. Alternatively, the entrance at the probe 1 may be off-center (e.g., away from the central axis of the probe 1).

Figure 22:
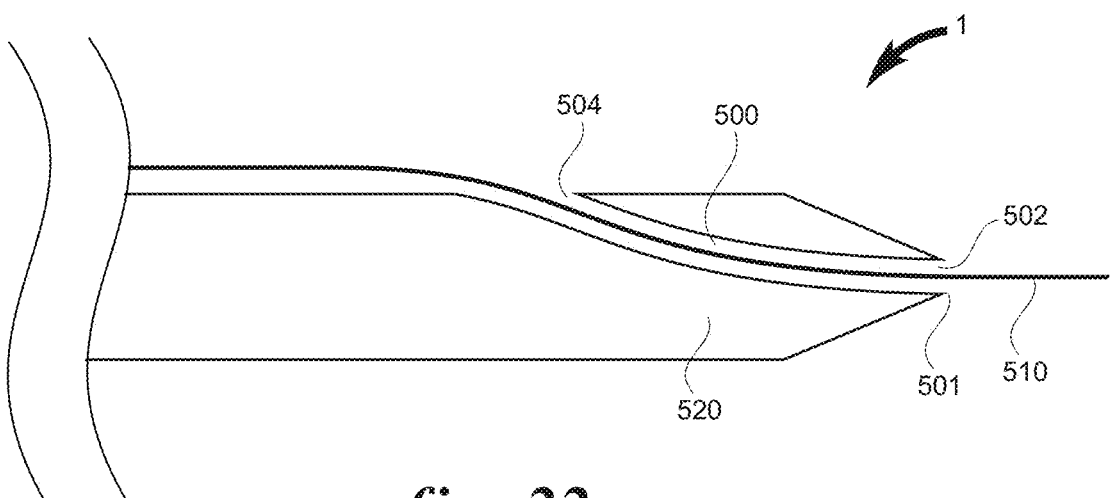
FIG. 22 illustrates an imaging device that includes a guidewire lumen in accordance with other embodiments.

In some embodiments, the lumen 500 may be defined by an internal guiding tube 520, where the guiding tube 520 is fixed within the distal section of the probe 1 by thermal fusion, thermal bonding, adhesive bonding, laser bonding, or any of other techniques (FIG. 22). The guiding tube 520 has a first end that provides the opening 501 at the distal tip 502, and a second end that provides the opening 504.

Figure 23:
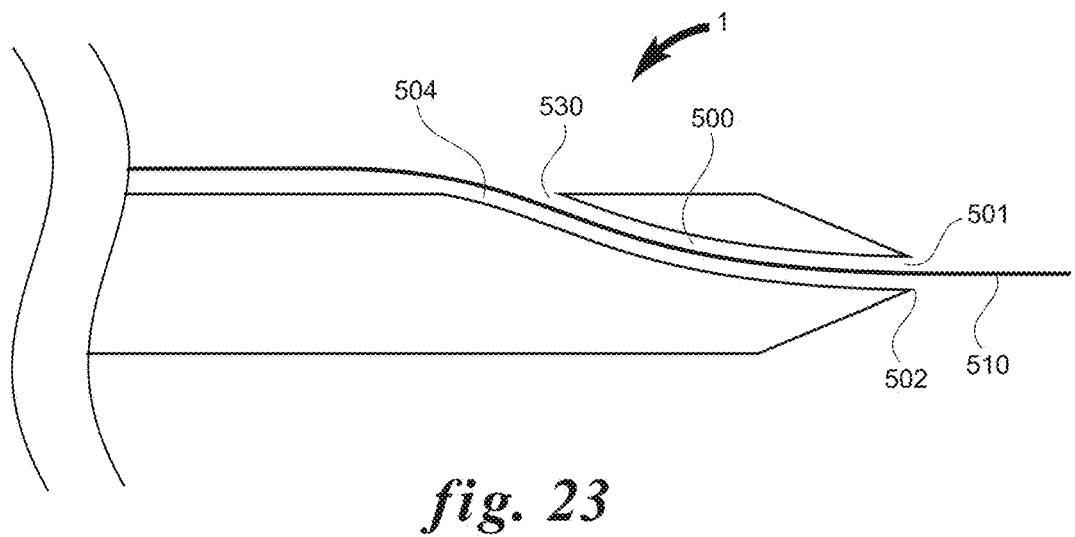
FIG. 23 illustrates an imaging device that includes a guidewire lumen in accordance with other embodiments.

In other embodiments, the lumen 500 in the probe 1 may be provided by a cutout 530 at the probe 1 (FIG. 23). In some embodiments, the distal portion of the probe 1 is solid, and the lumen 500 is provided by creating a cutout through the distal portion of the probe 1. In some cases, the cutout may be made in a molding process (e.g., the cutout may be internally molded). For example, the lumen 500 may be formed by molding a passage way using a mandrel, and then withdrawing the mandrel. Alternatively, a guiding tube (which may be machined, cast, or formed in place, etc.) may be placed at the distal section of the catheter sheath as to direct the guidewire 510 out to the side of the catheter. Such forming may be done by using UV curable adhesive and a mandrel, and allowing the UV curable adhesive to cure. The mandrel may then be removed, leaving a formed path for the guidewire 510 to enter and exit.

Figure 24:
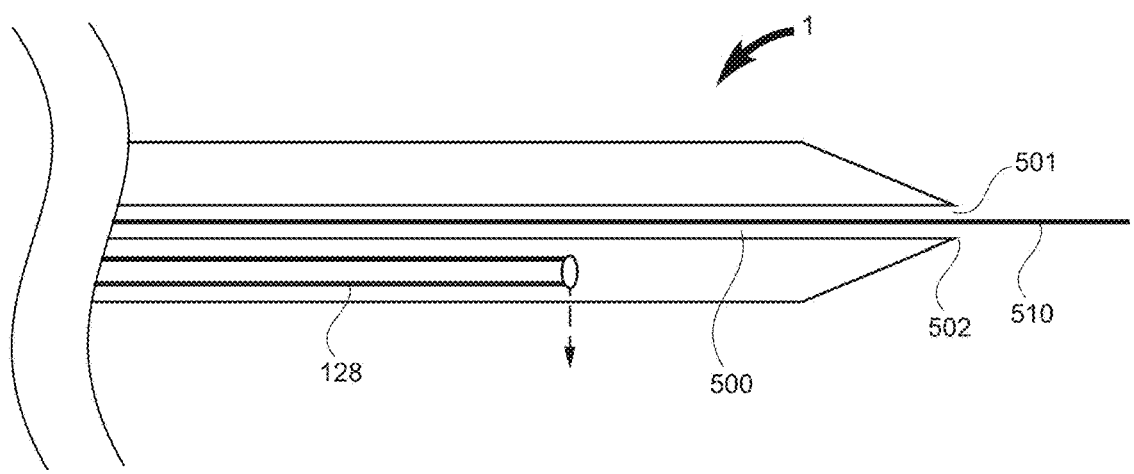
FIG. 24 illustrates an imaging device that includes a guidewire lumen in accordance with other embodiments.
Figure 25:
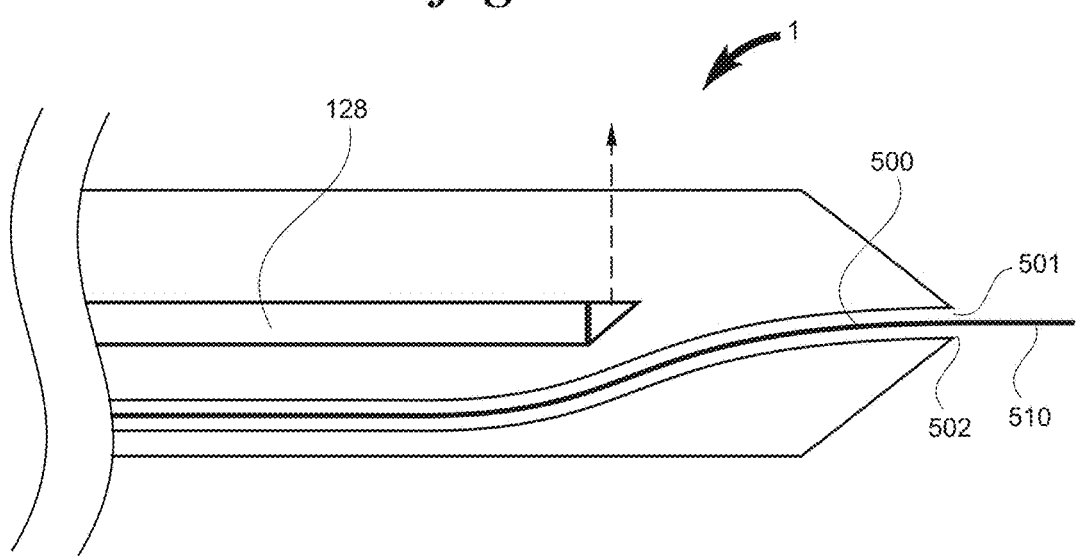
FIG. 25 illustrates an imaging device that includes a guidewire lumen in accordance with other embodiments.

In other embodiments, the lumen 500 may extend from the distal tip 502 towards the proximal end of the probe 1 in a direction that is parallel to a longitudinal axis of the probe 1 (FIG. 24). The lumen 500 may be along the central axis of the probe 1. In such cases, the imaging probe 1 is placed off the central axis relative to the center of the probe 1 (like that in an over-the-wire configuration). In other embodiments, the lumen 500 may be off-axis. In such cases, the opening 501 at the distal tip 502 may also be off-axis so that the lumen 500 including its distal section is completely off-axis. Alternatively, the opening 501 at the distal tip 502 may be at the center, and the majority of the lumen 500 is off-axis (FIG. 25). In such cases, the lumen 500 extends along a side of the probe 1 and transitions towards the center.

Figure 26:
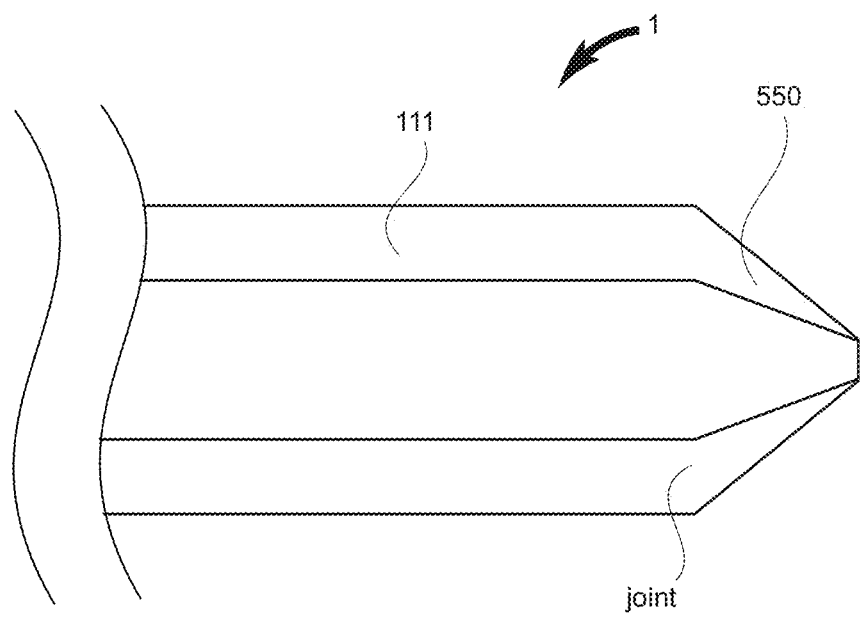
FIG. 26 illustrates an imaging device with a tip in accordance with some embodiments.

In some embodiments, the distal end of the probe 1 may include a tip 550 (e.g., a catheter tip) (FIG. 26). The tip 550 may be made from a soft, low durometer material as to provide a autramatic catheter tip. This may prevent perforating of the lumen or vessel in which the imaging probe 1 is being positioned. In other embodiments, the tip 550 may be made from a same material as that of the body of the probe 1. For example, the tip 550 may be thermally formed from the same material that is used to make the catheter sheath. In further embodiments, the tip 550 may be made from a material that is different from the catheter sheath. For example, the tip 550 may be made by injection molding, casting, thermal forming, compression bonding, or any of other known techniques. The tip 550 is then bonded to the catheter sheath by adhesive (e.g., UV curable adhesive), epoxy, thermal fusion bonding, butt bonding, or laser bonding.

Probe Construction

Figure 27:
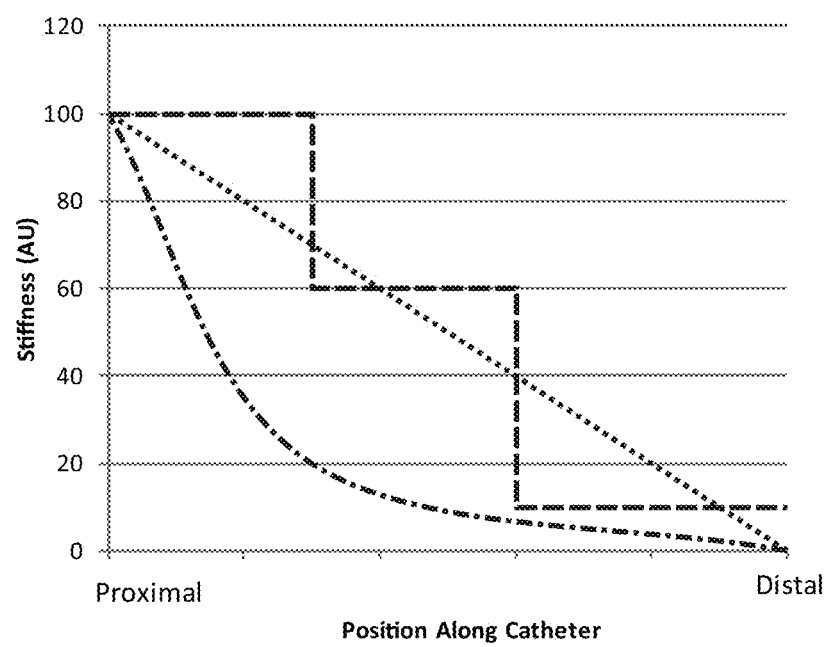
FIG. 27 illustrates a graph showing a stiffness profile of a tube in accordance with some embodiments.
Figure 28:
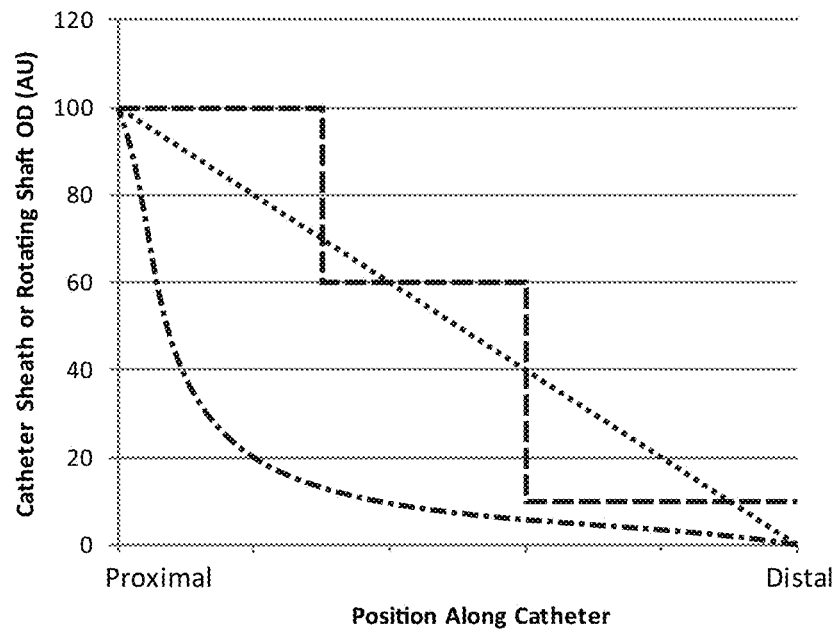
FIG. 28 illustrates a graph showing a wall thickness of a tube in accordance with some embodiments.
Figure 29:
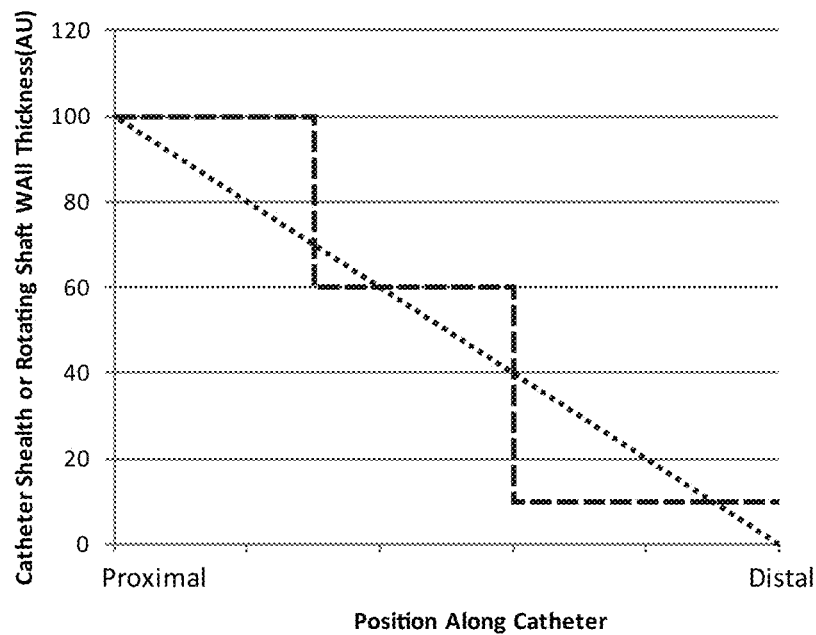
FIG. 29 illustrates a graph showing a cross sectional dimension profile of a tube in accordance with some embodiments.

In one or more embodiments, the tube 180 surrounding the optical waveguide 128 may have a constant stiffness. In other embodiments, the tube 180 may have variable stiffness from the proximal to distal section of the probe 1. This may be varied by varying the diameter or wall thickness of the tube 180 at various points or sections along the length of the imaging probe 1. For example, in some embodiments, the probe 1 may have two or more (e.g., 2, 3, 4, 5 or greater) sections from the proximal to distal section of the imaging probe, with decreasing stiffness (FIG. 27). In some embodiments, the variable stiffness of the tube 180 along the length of the probe 1 may be achieved by varying the diameter of the tube 180 (FIG. 28). In other embodiments, the stiffness of tube 180 along the length of the probe 1 may also be varied by varying the wall thickness of tube 180 (FIG. 29). By changing the stiffness of tube 180, the rotating shaft formed by tube 180, and/or the optical waveguide 128 comprising these elements, may have a stiffness at a distal section that is much less than the stiffness at a proximal section. In other embodiments, the optical waveguide 128 is not configured to transmit any force, and the tube 180 is configured to transmit all or most (e.g., 99%) of the force. In such cases, only the tube 180 functions as the rotating shaft.

In the above embodiments, the tube 180 is illustrated as surrounding the optical waveguide 128 and is spaced away from the optical waveguide 128. In other embodiments, the tube 180 may be directly or indirectly coupled to the exterior surface of the optical waveguide 128. For example, in some embodiments, the tube 180 may be frictionally engaged with the exterior surface of the optical waveguide 128. In other embodiments, the tube 180 may be glued to the exterior surface of the optical waveguide 128. In further embodiments, there may be one or more layers disposed between the exterior surface of the optical waveguide 128 and the tube 180. Also, in one or more embodiments, the tube 180 may be considered to be a part of an optical cable that includes the optical fiber core 142.

Figure 30A:
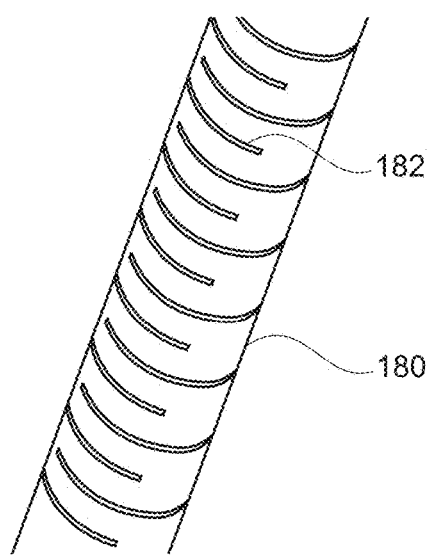
FIGS. 30A-30P illustrate different cutout configurations at a tube in accordance with different embodiments.
Figure 30B:
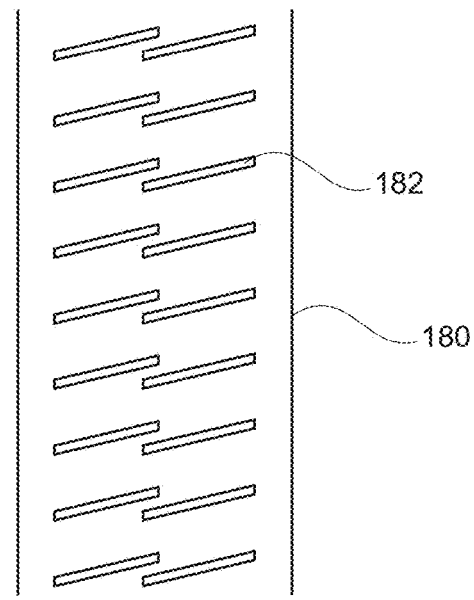
Figure 30C:
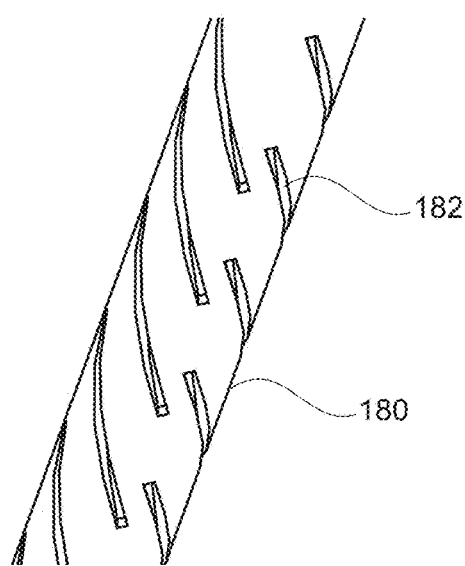
Figure 30D:
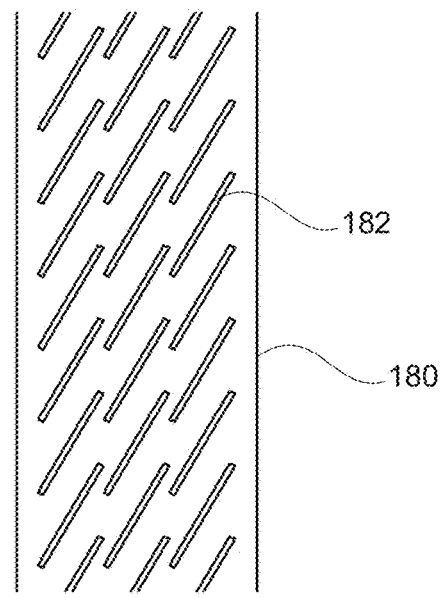
Figure 30E:
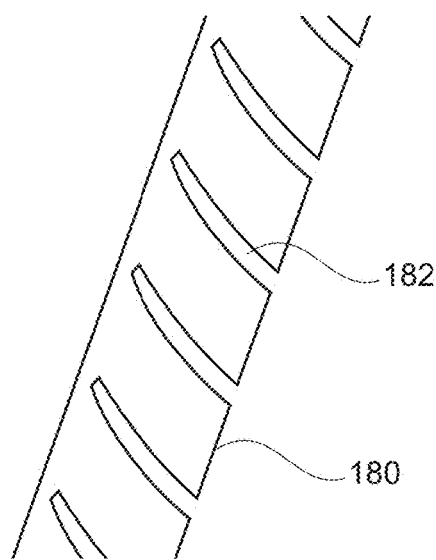
Figure 30F:
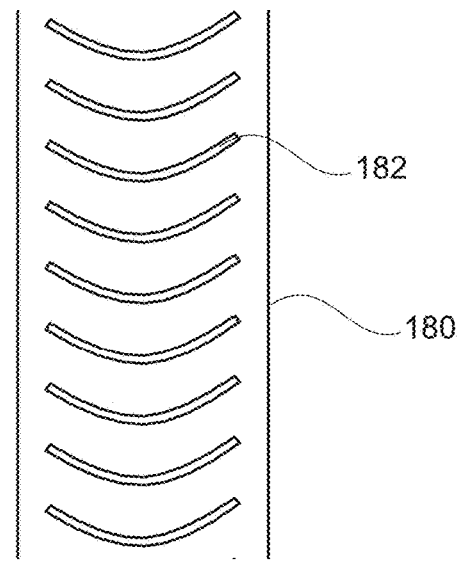
Figure 30G:
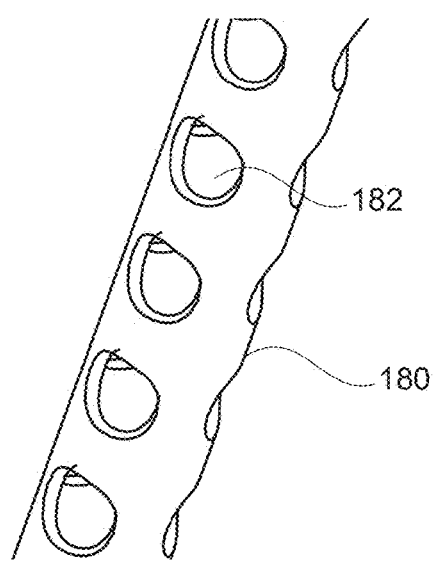
Figure 30H:
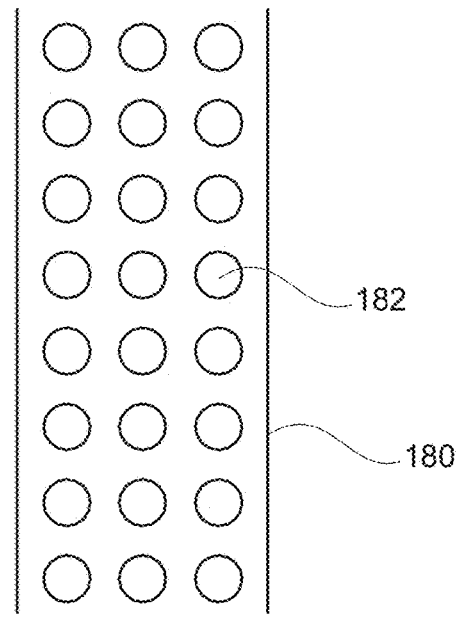
Figure 30I:
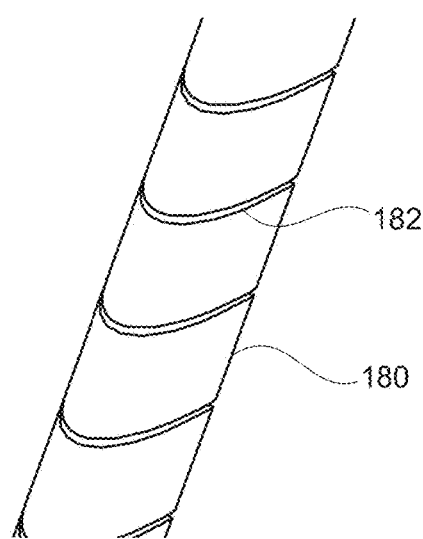
Figure 30J:
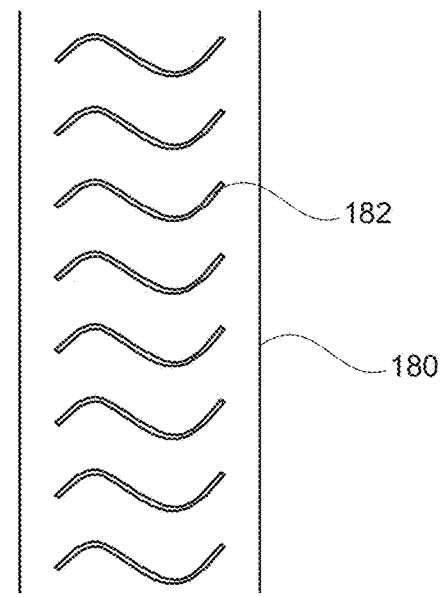
Figure 30K:
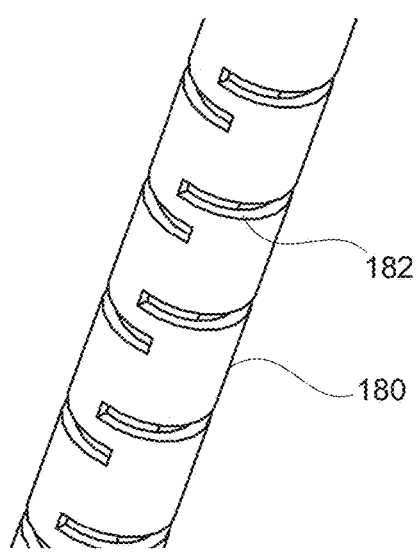
Figure 30L:
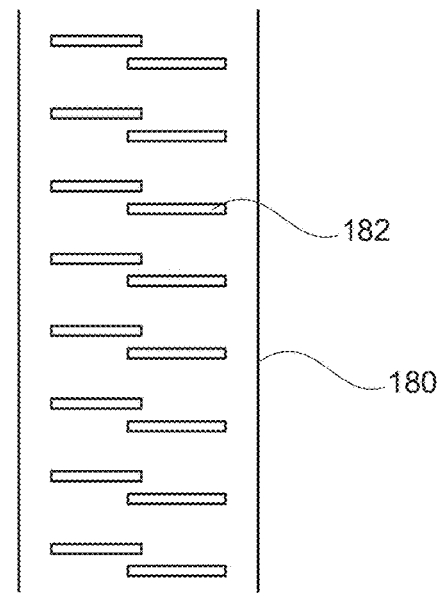
Figure 30M:
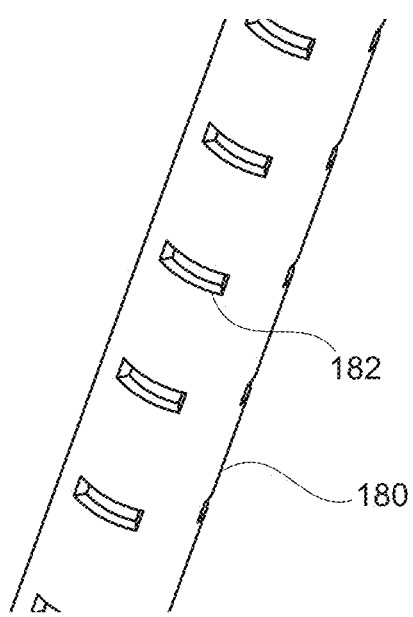
Figure 30N:
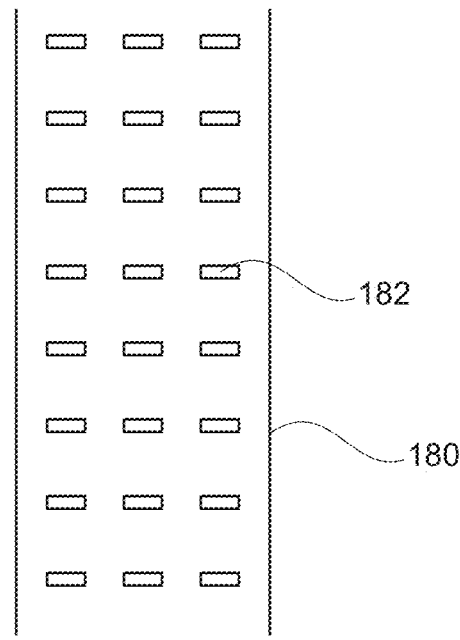
Figure 30O:
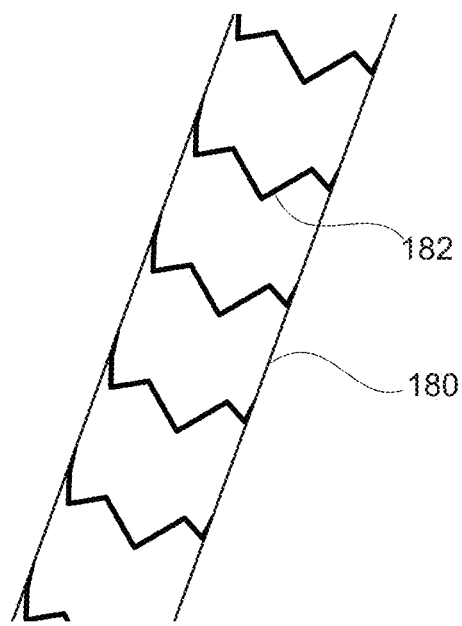
Figure 30P:
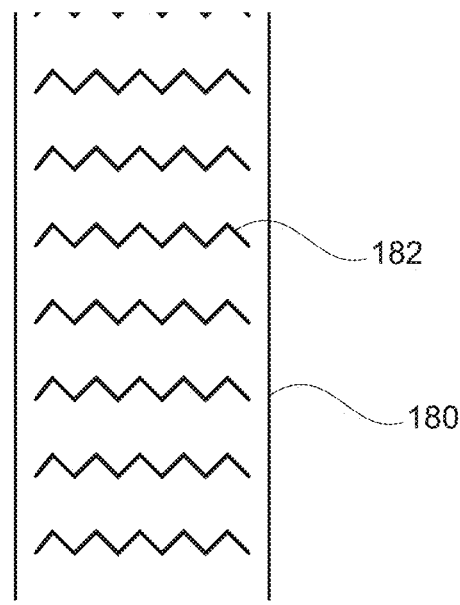

In further embodiments, the variable stiffness along the length of the tube 180 may be achieved by providing openings or cutouts through the wall of the tube 180. FIG. 30A-30P illustrate different variations of the tube 180 with different respective cutout configurations in different embodiments. FIG. 30A shows the tube 180 having cutouts 182, wherein each cutout 182 has an elongate configuration. In the illustrated embodiments, each cutout 182 has a rectilinear shape (which viewed from a side of the tube 180), and has an axis that is perpendicular to a longitudinal axis of the tube 180. Also, the cutouts 182 are staggered in the illustrated embodiments. In other embodiments, each cutout 182 may have an axis that forms a non-perpendicular angle with the longitudinal axis of the tube 180 (FIG. 30B).

Also, in other embodiments, the length of the cutouts 182 may be different from that shown. For example, as shown in FIG. 30C, in other embodiments, the length of the slanted cutouts 182 may be shorter or longer than that shown in FIG. 30B. FIG. 30D is the tube 180 of FIG. 30C that has been unfolded or flattened out to show the size and orientation of the cutouts 182 more clearly.

In further embodiments, the cutouts 182 may be non-staggered. FIG. 30E shows the cutouts 182 arranged in a non-staggered configuration, wherein each cutout 182 has a curvilinear configuration. FIG. 30F is the tube 180 of FIG. 30E that has been unfolded or flatten out to show the size and orientation of the cutouts 182 more clearly.

In still further embodiments, the cutouts 182 may have a non-elongate shape. For example, in other embodiments, the cutouts 182 may be circular openings arranged in rows and columns (FIG. 30G). FIG. 30H is the tube 180 of FIG. 30G that has been unfolded or flatten out to show the size and orientation of the cutouts 182 more clearly. In other embodiments, the cutouts 182 may be rectangular or square openings arranged in rows and columns (FIG. 30M). FIG. 30N is the tube 180 of FIG. 30M that has been unfolded or flatten out to show the size and orientation of the cutouts 182 more clearly.

In other embodiments, each cutout 182 may have a curvilinear shape. FIG. 30I shows each cutout 182 having a sinusoidal or wavy configuration. FIG. 30J is the tube 180 of FIG. 30I that has been unfolded or flatten out to show the size and orientation of the cutouts 182 more clearly.

It should be noted that the gap of the cutout 182 may have different sizes in different embodiments, and that the cutout 182 is not limited to the examples shown. For example, as shown in FIG. 30K, in other embodiments, the cutouts 182 may each have a width that is wider than that shown in FIG. 30A. FIG. 30L is the tube 180 of FIG. 30K that has been unfolded or flatten out to show the size and orientation of the cutouts 182 more clearly.

In other embodiments, each cutout 182 may have a customized shape. FIG. 30O shows each cutout 182 having a zig-zag configuration. FIG. 30P is the tube 180 of FIG. 30O that has been unfolded or flatten out to show the size and orientation of the cutouts 182 more clearly.

The cutouts may be accomplished in a number of ways. In some embodiments, the cutouts maybe cut using a band saw, circular saw, or other fine tooth cutting blade. In other embodiments, the cutouts maybe cut using an abrasive cutting wheel, abrasive wire saw, diamond saw, or wafer dicing saw. In further embodiments, the cutouts may also be cut using electronic discharge machining (EDM) or electrochemical milling. Further methods of creating the cutouts include laser cutting using a femtosecond, picosecond, nanosecond, or other pulsed or continuous wave laser. In still further embodiments, the cutouts may be formed by a stamping or punching process. In other embodiments, the cutouts maybe further cut using a lathe, milling machine, or other computer controlled cutting equipment.

It should be noted that the cutouts 182 are not limited to the examples described, and that the cutouts 182 may have different configurations in different embodiments. For example, in other embodiments, the cutouts 182 may each have a size and/or orientation that is different from the examples described. Also, in other embodiments, the amount of overlapping between adjacent cutouts 182 may be different from the examples described. Also, in further embodiments, the number of cutouts 182 per unit length of the tube 180 may be different from the examples described.

In one or more embodiments, the cutouts 182 allow the tube 180 to transmit torque and axial load efficiently, while allowing the tube 180 to bend easily. In some embodiments, the tube 180 with the cutouts has a torsional stiffness that is at least 0.00001 newton/meter$^2$ (e.g., 0.000019 newton/meter$^2$). Also, in some embodiments, the tube 180 with the cutouts has an axial stiffness (longitudinal stiffness) that is at least 0.001 newtons (e.g., 0.00147 newtons). In other embodiments, the torsional stiffness and/or the axial stiffness may be different from the examples described.

In addition, in some embodiments, the tube 180 with the cutouts allows at least a distal section of the tube 180 to have a bending stiffness (flexural stiffness) that is at most 70000000 newton/meter$^2$ (e.g., 68947572.9 newton/meter$^2$). In other embodiments, the bending stiffness may be different from the example described. Furthermore, in some embodiments, the tube 180 with the cutouts may allow any combination of the above features to be achieved.

Figure 31:
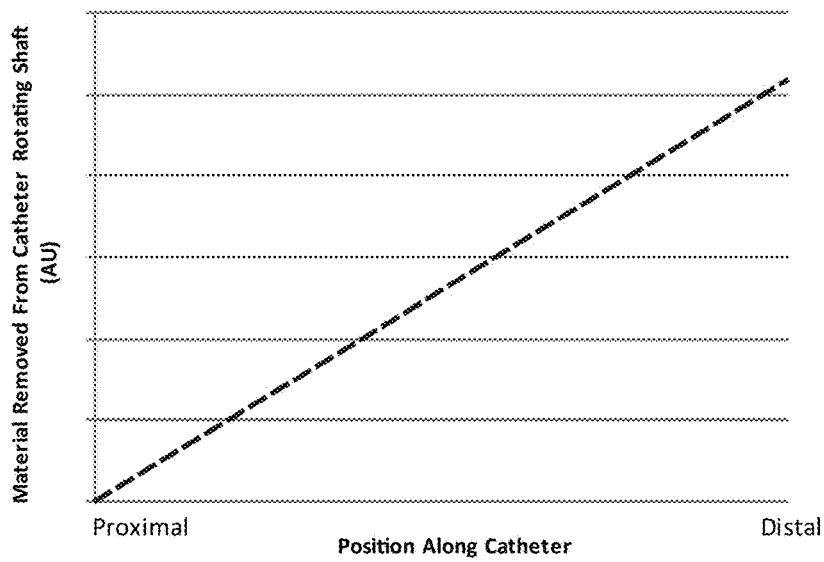
FIG. 31 illustrates a graph showing a variation of an amount of cutout materials along a length of a tube in accordance with some embodiments.

As shown in FIG. 31, in some embodiments, the stiffness of the tube 180 along its length may be variable by varying an amount of cutouts along the length of the tube 180. For example, in some embodiments, the amount of cutouts (e.g., material removed from tube 180) at the distal section of the tube 180 may be more compared to a relatively proximal section of the tube 180, thereby making the distal section more flexible than the relatively proximal section.

Figure 32:
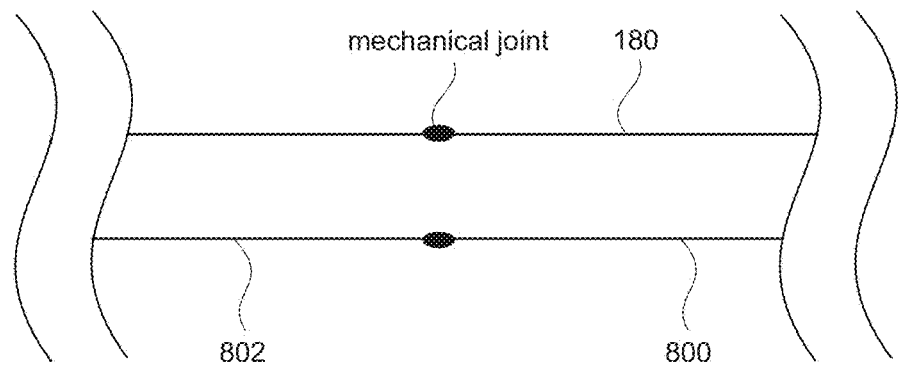
FIG. 32 illustrates a construction of a rotating shaft in accordance with some embodiments.

In other embodiments, the flexibility of the rotating shaft may be modulated along its length by constructing the tube 180 using different materials. For example, in some embodiments, the tube 180 may be formed by joining a polymer tube 800 to a metal hypotube 802 by bonding, adhesive, welding, crimping, swaging, laser bonding, epoxying, or any of other techniques (FIG. 32). Such configuration may allow a stiffness of the probe 1 at a distal section to be less compared to a proximal section. The polymer tube 800 may have cutouts as similarly discussed. In other embodiments, the polymer tube 800 may also have braids of wire orientated in a criss cross, or spiral pattern to provide a modulated stiffness from the proximal to distal end of the rotating shaft. In some embodiments, the distal tubing 800 may have a length that is anywhere from 6 inches to 30 inches. In other embodiments, the distal tubing 800 may be longer than 30 inches, or may be less than 6 inches.

Figure 33:
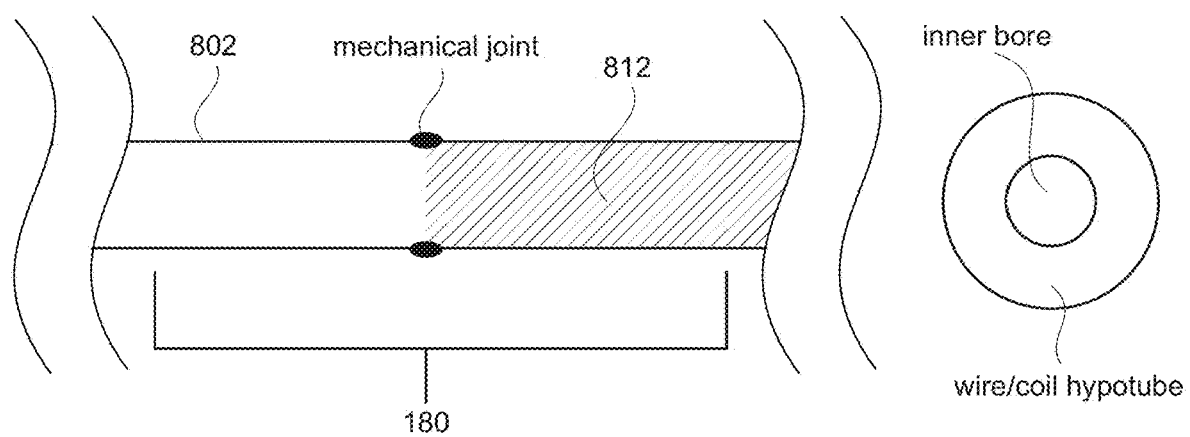
FIG. 33 illustrates a construction of a rotating shaft in accordance with other embodiments.

In other embodiments, the tube 180 may include a coil of wire or braided tubing 812 that is attached to a more rigid hypotube 802 located at a more proximal end of the imaging probe 1 (FIG. 33). In some embodiments, the distal tubing 812 may have a length that is anywhere from 6 inches to 30 inches. In other embodiments, the distal tubing 812 may be longer than 30 inches, or may be less than 6 inches. In some embodiments, the coil at the distal tubing 812 may have a wire diameter that is anywhere from 50 um to 300 um, and the resulting coil may have a diameter that is anywhere from 100 um to 10000 um. In other embodiments, the coil may have other diameters that are different from those described, and the resulting coil may have other diameters that are different from those described. In some embodiments, the wire diameter may vary along the length of the wire, and/or a pitch of the coil formed by the wire may vary along a length of the coil, to decrease the stiffness of the coil from the proximal end to distal end.

In some embodiments, the design of the imaging probe (e.g., catheter) 1 may consider the shaft pushability, the shaft torquability, and/or the shaft bending stiffness.

Shaft pushability is the response of the shaft where a force is applied in a direction that is along the rotational axis of the shaft. The shaft pushability may be modeled as an axial stiffness of the shaft, which is defined as $k_{axial}=EA/L$, where $k_{axial}$ is the axial stiffness, E is the modulus of elasticity, where A is the cross-sectional area, and L is the length of the shaft. In some embodiments, the shaft pushability may be increased by increasing $k_{axial}$, which may be achieved by reducing the catheter length L, increasing the modulus of elasticity E of the shaft material, and/or increasing (e.g., maximizing) the cross sectional diameter of the shaft. The shaft pushability efficiency may be defined as the percentage of force transmitted from the proximal to distal end of the shaft. In some embodiments, the pushability efficiency of the shaft 180 may be greater than 0.1 percent, 1 percent, 10 percent, 20 percent (such as 21-50 percent, or 50-100 percent).

Shaft torquability is the response of the shaft to an applied torque placed about the rotational axis of the shaft, which causes an angular rotation of the shaft relative from the proximal and distal ends. A shaft torquability may be modeled as a torque stiffness: $k_{torq}=GJ/L$, where $k_{torq}$ is the torque stiffness, G is the shear modulus, J is the polar moment of inertia, and L is the length of the shaft. Shaft torquability may be improved by increasing the torque stiffness $k_{torq}$, which may be achieved by increasing the polar moment of inertia J for a tubular shaft, increasing the shear modulus G, and/or reducing the length L of the shaft. The polar moment of inertia J for a tube is $J=\pi/32$ $(do^4-di^4)$, where do is the shaft's outer diameter, and di is the shaft's inner diameter. In some cases, J may be increased by increasing the outer diameter and/or wall thickness of the tubular shaft.

In some cases, due to the torsiorial strain undergone by the rotating shaft 180 or optical waveguide 128, these components may experience phase lag and angular displacement. In some embodiments, the shaft 180 is made sufficiently stiff in torsion, so that the phase lag and angular displacement of the rotating shaft 180 and the optical waveguide 128 is less than 360 degrees, more preferably less than 90 or 180 degrees, even more preferably less than 10 degrees, and most preferably less than 0.36 degrees or 0.036 degrees.

Shaft bending (or flexural) stiffness may be modeled as a clamped beam system (e.g., fixed at both ends of a beam), in which the beam is subject to a downward force at the midsection of the beam. At small deflections, the beam (e.g., the tubing) behaves as a spring system, and the flexural stiffness may be represented as $k_{flexural}=3EI/L^3$, where $k_{flexural}$ is the bending stiffness, E is the modulus of elasticity, I is the moment of inertia, and L is the length of the shaft. In some embodiments, the flexural stiffness of the shaft may be reduced by reducing $k_{flexural}$, which may be achieved by reducing the moment of inertia I, reducing the modulus of elasticity E, and/or reducing the length L. In some embodiments, for a shaft with a circular cross section, $I=\pi/64$ $(do^4-di^4)$, where do is the tube's outer diameter and di is the tube's inner diameter. In some embodiments, reduction of the moment of inertia I may be achieved by reducing the outer diameter and/or the wall thickness of the shaft.

Figure 34:
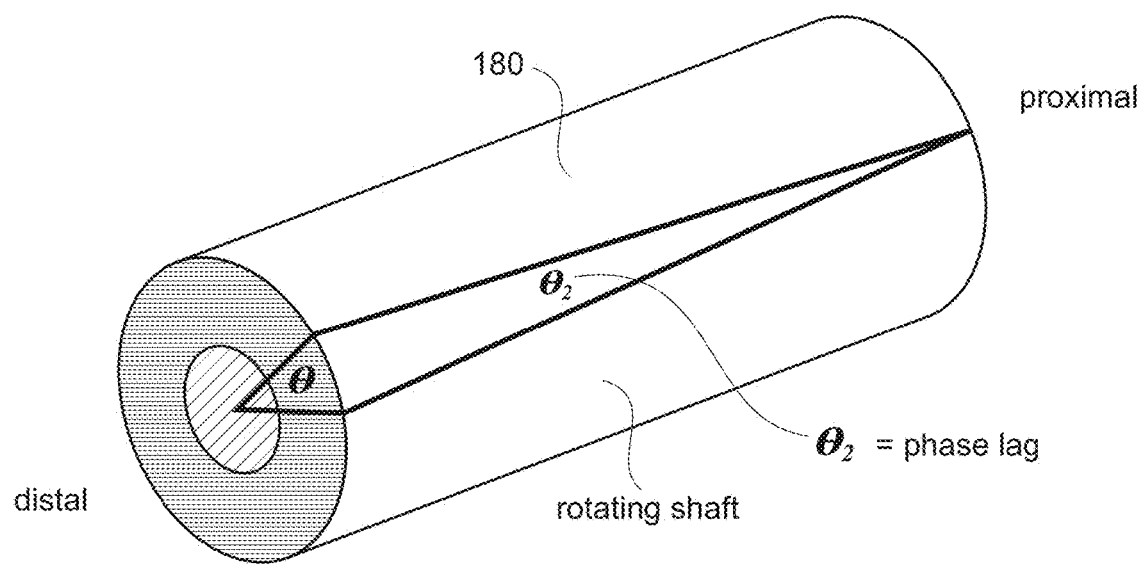
FIG. 34 illustrates a phase lag due to torsional strain.
Figure 35:
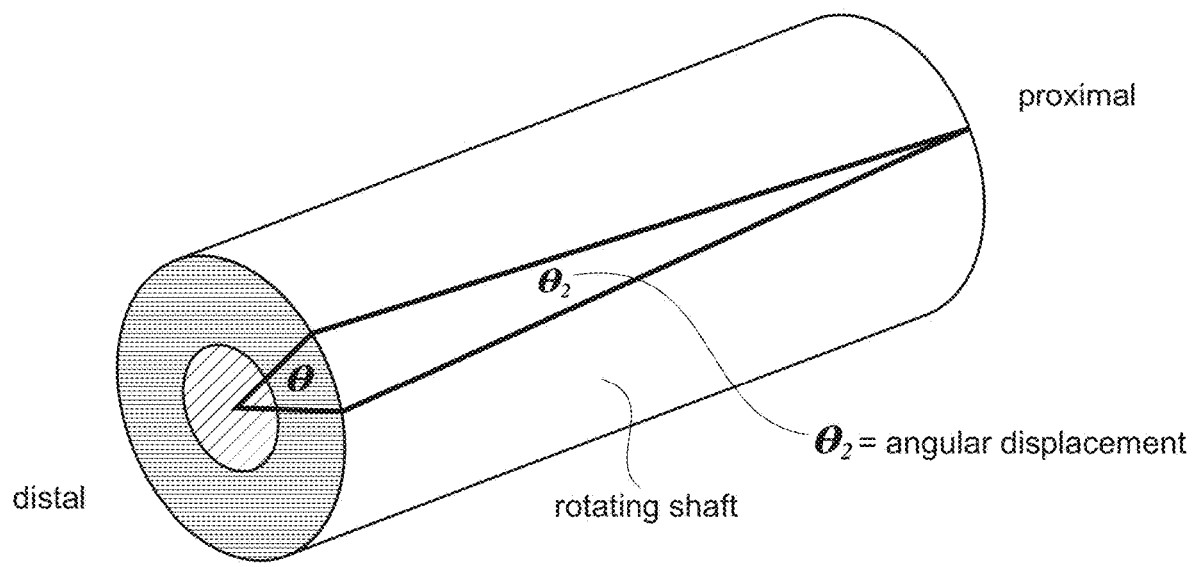
FIG. 35 illustrates an angular displacement due to torsional strain.

In some embodiments, the rotating shaft 180 may have a first section (e.g., a section near the distal end) with a first bending stiffness, and a second section (e.g., a section proximal to the first section) with a second bending stiffness higher than the first bending stiffness. Thus, such rotating shaft may have a distal section that is more flexible than a proximal section. If torque stiffness and/or torque transfer efficiency is not considered in the design of the rotating shaft 180, such configuration may limit the rotating shaft's ability to transmit torque from the proximal end to the distal end. This may result in a rotational phase lag (FIG. 34), or a rotational displacement (FIG. 35) from the proximal to distal end. This is undesirable since it may cause non uniform rotational distortion of the image. Thus, in one technique for designing the shaft 180, it may be desirable to maximize the torsional stiffness, which may provide a desired torque transfer efficiency, and may reduce phase lag and rotational displacement of the rotating shaft from the proximal end to distal end of the rotating shaft to acceptable levels. In some embodiments, the shaft 180 may have a torque transfer efficiency (defined as the torque transmitted to the distal end divided by the torque applied at the proximal end) that is higher than 50%, and more preferably higher than 60%, and more preferably higher than 80%, and more preferably higher than 90%, and even more preferably higher than 95% (e.g., 99%). At the same time, at the proximal section (e.g., the proximal 1/10, or longer, of the length) of the imaging probe 1 where the connector is located, the bend radius of the shaft 180 (and the catheter sheath) can be almost infinite, or a large number greater than 1 mm, 10 mm, 100 mm, 1000 mm, etc. At the midsection of the catheter, the bend radius may be anywhere from 10 mm to 100 mm, more preferably anywhere from 10 mm to 50 mm, and even more preferably anywhere from 10 mm to 20 mm. At the distal section (e.g., the distal 1/3 of the length) of the catheter, the bend radius of the shaft 180 may be anywhere from 1 mm to 100 mm, more preferably anywhere from 1 mm to 20 mm, and even more preferably anywhere from 1 mm to 10 mm.

In some embodiments, the rotating shaft 180 may have a length L that is anywhere from 10 mm-10 m. In some embodiments, for such a length of the rotating shaft, the axial stiffness may be at least 0.00147 to 4.5 newtons, the torsional stiffness may be at least 0.000019 newton/meter², and/or the bending stiffness may be at most 70000000 newton/meter² at the distal most 1/3 of the length L. In other embodiments, the axial stiffness, torsional stiffness, and the bending stiffness may have respective values that are different from the examples described. In some embodiments, a finite element analysis program, such as Ansys, ABAQUS, COMSOL, or other mechanical analysis software, may be used to design the desired characteristics of the rotating shaft.

In some embodiments, at the proximal section (e.g., the proximal 1/10, or longer, of the length) of the imaging probe 1 where the connector is located, the bend radius of the probe 1 can be almost infinite, or a large number greater than 1 mm, 10 mm, 100 mm, 1000 mm, etc. At the midsection of the probe 1, the bend radius may be anywhere from 10 mm to 100 mm, more preferably anywhere from 10 mm to 50 mm, and even more preferably anywhere from 10 mm to 20 mm. At the distal section (e.g., the distal 1/3 of the length) of the probe 1, the bend radius may be anywhere from 1 mm to 100 mm, more preferably anywhere from 1 mm to 20 mm, and even more preferably anywhere from 1 mm to 10 mm. In some embodiments, this may be achieved by using different sheath diameters and wall thickness, as well as bonding or welding different durometer tubing together to create a modulated stiffness of the catheter sheath. The catheter sheath may also have bonded or welded together sections of dissimilar polymer materials or compositions to achieve the desired characteristics.

Also, in some embodiments, the rotating shaft 180 located at the rotary optical waveguide joint at the proximal end of the probe 1 may be made substantially stiffer the other parts of the rotating shaft 180, particularly the distal section of the rotating shaft 180. Furthermore, the very proximal section of the shaft 180 should have a sufficient bending stiffness such that when the shaft 180 is pulled back, the shaft 180 does not sag as to cause inadvertent pullback on the imaging probe 1, which may result in positioning error of the location of imaging. This may be achieved by having a large diameter tube at the very proximal end made from stainless steel and having a diameter of at least 400 microns, 1000 microns, 2000 microns, or even greater than 2000 microns. This section of the proximal rotating shaft 180 may be polished, or purposely roughened to provide a low frictional and low adhesion mating surface and for rotation and imaging pullback.

Figure 36:
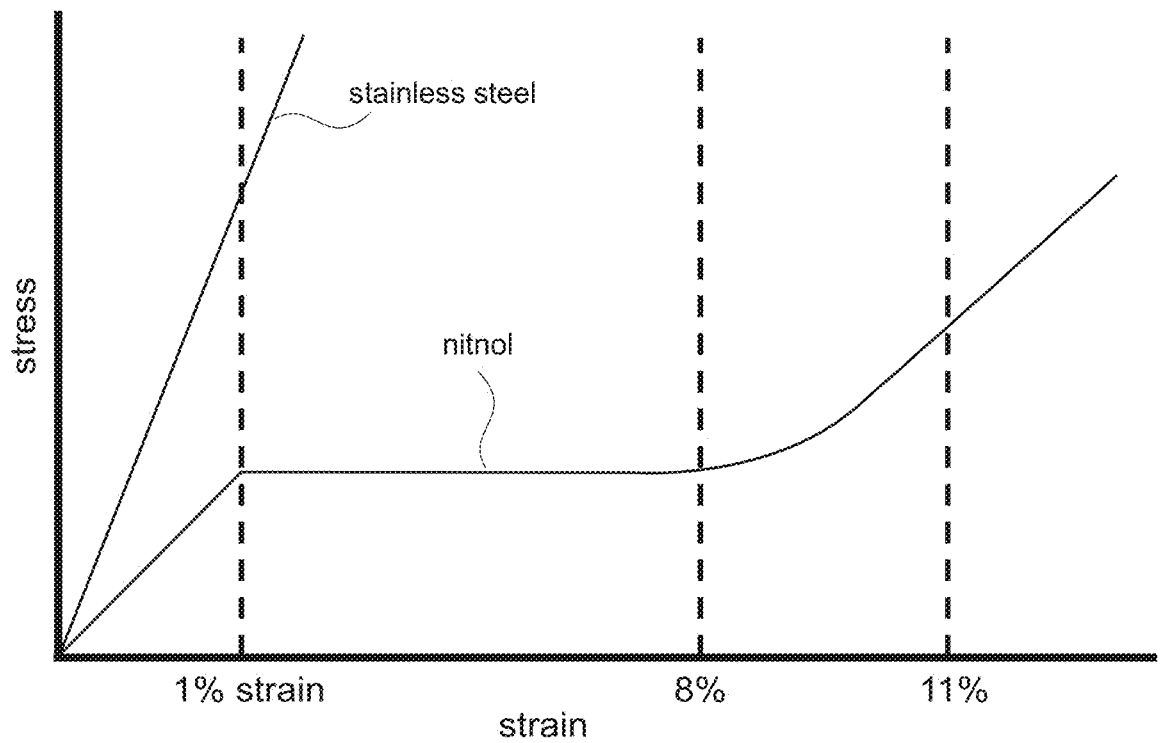
FIG. 36 illustrates a stress-strain curve for Nitinol and stainless steel.

In some embodiments, at least a portion of the rotating shaft may be made from stainless steel. For example, in some embodiments, a proximal portion (e.g., the proximal end) of the rotating shaft may be made from stainless steel, while the distal portion of the rotating shaft may be made from a relatively more flexible material. In other embodiments, Nitinol may be used to make the rotating shaft. Nitinol is a super-elastic metal which enables very high strains up to 8% to 11%. The stress-strain curve for Nitinol has a section where the stresses remain constant for strains between 1-8 percent, thus enabling the Nitnol rotating shaft to be highly flexible (FIG. 36).

Figure 37:
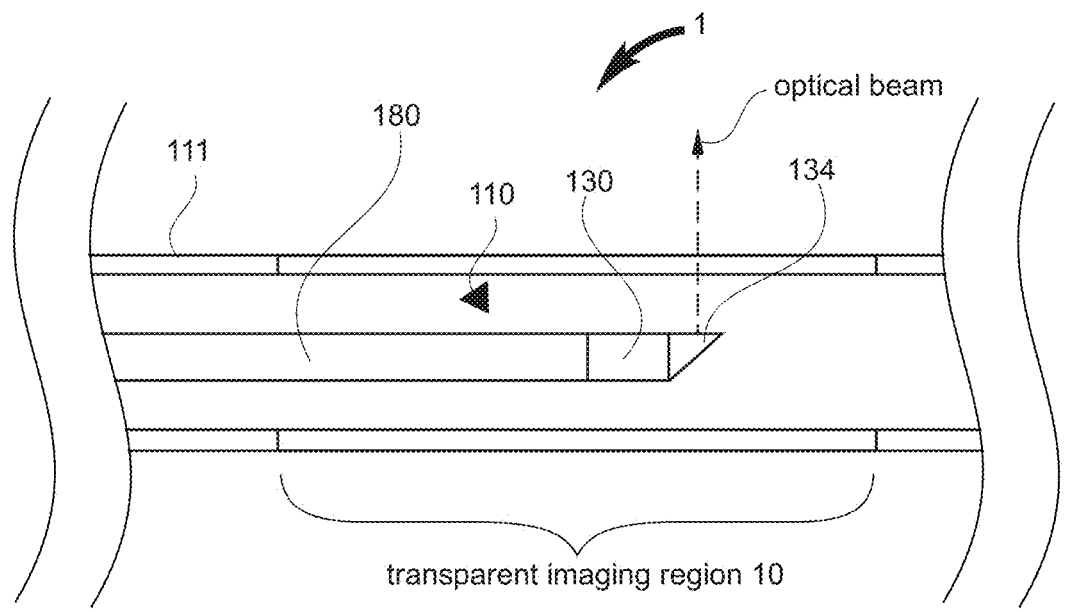
FIG. 37 illustrates an imaging probe having a transparent imaging region in accordance with some embodiments.

In some embodiments, the window 10 of the imaging probe 1 may be transparent to the optical wavelengths of operation. These wavelength ranges may range from 200 nm-11000 nm, preferably 500-2000 nm, and more preferably 800-1600 nm, and most preferably 1100 nm-1400 nm. Also, in some embodiments, the window 10 may have a length along the longitudinal axis of the probe 1 that is sufficiently long to accommodate a range of translation of the optics 134 (FIG. 37). The translation of the optics 134 may be accomplished manually in some embodiments by pushing the component 110 relative to the catheter sheath to advance the optics 134 relative to the catheter sheath, or by pulling the component 110 relative to the catheter to retract the optics 134 relative to the catheter sheath. In other embodiments, the advancement and retraction of the component 110 relative to the catheter sheath may be performed using a positioner, which mechanically moves the component 110 relative to the catheter sheath. In an imaging technique, translational movement of the optics 134 relative to the catheter sheath is advantageous. For example, in some cases, the catheter sheath may be maintained stationary relative to a body lumen (e.g., a blood vessel). Then the shaft 180 with the optics 134 may be moved axially along the length of the probe 1 relative to the window 10 to image different portion of the tissue along the length of the body lumen. This technique may reduce an amount of rubbing against the wall of the body lumen by the probe 1.

Furthermore, in some embodiments, the shaft 180 may be designed such that when the shaft 180 is pulled, the shaft 180 does not stretch an excessive amount as to cause mechanical failure of the optical waveguide 128, damage of optics, or debonding of optical components. A reduction of stretching may reduce sample arm length changes in the optical imaging system and also reduces polarization differences between sample and reference arms of the interferometer of the optical system. In some embodiments, an amount of stretching undergone by the rotating shaft should be less than 0.05 inch, and more preferably less than 0.005 inch, and even more preferably less than 0.001 inch, and even more preferably 0.0005 inch or less.

Also, in some embodiments, the stiffness of the probe 1 may be approximated by summing the stiffness of the catheter sheath and the stiffness of the rotating shaft 180. In some embodiments, at the very proximal section of the imaging probe 1 where the connectors are located, the bend radius may be almost infinite, or a large number greater than 1 mm, 10 mm, 100 mm, 1000 mm, etc. At the midsection of the probe 1, the bend radius achievable may be anywhere from 10 mm to 100 mm, and more preferably anywhere from 10 mm to 50 mm, and even more preferably anywhere from 10 mm to 20 mm. At the distal of the probe 1, the bend radius achievable may be anywhere from 1 mm to 100 mm, and more preferably anywhere from 1 mm to 20 mm, and even more preferably anywhere from 1 mm to 10 mm, while having a torque transfer efficiency that is higher than 50%, and more preferably higher than 60%, and more preferably higher than 80%, and more preferably higher than 90%, and even more preferably higher than 95% (e.g., 99%).

Lens and Gaussian Beam Theory

In some embodiments, the optics in the probe 1 may be configured to operate based on a Gaussian beam theory. A Gaussian beam propagating in free space has spot size w(z), and is smallest with the minimum value $w_0$ at the beam waist. The beam spot size as a function of wavelength $\lambda$ as a function of distance z along the optical beam path from the beam waist may be represented by the equation:

$$w(z) = w_0 \sqrt{1 + \left(\frac{z}{z_R}\right)^2}$$

where the z-axis is coincident or located at the beam waist, where w is the width of the beam, and $Z_R$ is the Rayleigh length (or also known as Rayleigh range). $Z_R$ may be represented by the equation:

$$Z_R = \pi W_0^2 / \lambda$$

The Rayleigh length (also referred to as Rayleigh range) is the distance along the optical axis or beam propagation path from the beam waist to where the beams area cross section is twice that of the waist beam area.

The confocal parameter b, also referred to as the depth of focus, is double the Rayleigh length, and may be expressed as:

$$b = 2z_R = \frac{2\pi w_0^2}{\lambda}$$

The beam divergence angle $\theta_{div}$ of the Gaussian beam may be expressed as a function of the Rayleigh length:

$$\theta_{div} = 2\frac{w_0}{z_R}$$

The diameter of the beam D located at the beam waist may be calculated as:

$$D = 2w_0 = \frac{4\lambda}{\pi \theta_{div}}$$

where $\lambda$ is the wavelength of light.

Gradient Index Lens Theory

In some embodiments, using a ray transfer matrix, also known as the ABCD matrix, analytic expressions for a given gradient index lens system may be created. A Gaussian beam may be expressed at a transverse plane with complex parameter $$q = z_d + i z_0$$

where $z_d$ is the distance of the transverse plane to the beam focus, and $z_0$ is the Rayleigh range. A Gaussian beam expressed as $q_1$ may be optically passed through optical components, which may be represented by the ABCD matrix, where in the ABCD matrix mathematically describes the optical element (e.g., lens, prism, mirror, etc.). The complex parameter $q_2$ of the beam in output plane may be expressed by $$q_2 = \frac{A q_1 + B}{C q_1 + D}$$

In modeling the lens system, it is first modeled from the beam exit from an optical waveguide such as a single mode optical fiber, and assumed that the beam waist at the plane located at the end of the single mode optical fiber is the smallest and in focus, where:

$$q_1 = iz_{01} = \frac{\pi n_f w_0^2}{\lambda} = \frac{n_f i}{a_0} = \frac{i}{a}$$

and where $z_{01}$ is the Rayleigh range of the first Gaussian beam, and a is defined as its inverse. The term of is the refractive index of the optical fiber core, $w_0$ is the beam radius located at the fiber core, and $\lambda$ is the wavelength of the optical beam guided by the optical fiber.

The optical gradient index lens system (or Gaussian lens system) may be modeled using the ABCD matrix, with sequential matrices for each optical component that the optical beam traverses to. The complex beam parameter of the optical beam at the output plane of each component may be expressed as:

$$q_2 = \frac{AC + BDa^2}{C^2 + D^2 a^2} + i\frac{(AD-BD)a^2}{C^2 + D^2 a^2}$$

For the complex parameter, working distance (WD) and expressed as $z_w$ may be calculated by computing the negative of its real part:

$$z_w = \frac{AC + BDa^2}{C^2 + D^2 a^2}$$

$$z_{02} = \frac{(AD-BD)a^2}{C^2 + D^2 a^2}$$

With the derived expressions above, the imaginary part of $q_2$ also describes the new Rayleigh range $z_{02}$ at the focal length, which is the beam waist at the focal length. Beam waist $w_{02}$ expressed as the initial waist may be represented by:

$$w_{02} = w_{01}\left(\frac{n_f a z_{02}}{n_s}\right)^{1/2} = w_{01} a_0 \left[\frac{1}{n_s n_f}\frac{(AD-BC)}{C^2 + D^2 a^2}\right]^{1/2},$$

where $w_{01}$ is the initial beam waist in the input plane, and $n_s$ is the refractive index of the material directly located at the exit or output plane of the optical system.

Grin Lens Example

In some embodiments, a single mode optical fiber may be coupled with a spacer made from an optically transparent material that has a given length, and is coupled with a grin lens with a given length, with a prism bonded to the optical output end of the grin lens. Such optical system may be modeled as:

$$\begin{pmatrix} A & B \\ C & D \end{pmatrix} = \begin{pmatrix} 1 & z_w \\ 0 & 1 \end{pmatrix}\begin{pmatrix} 1 & 0 \\ 0 & \frac{n_1}{n_g} \end{pmatrix}\begin{pmatrix} 1 & l_1 \\ 0 & 1 \end{pmatrix}$$

-continued $$\begin{pmatrix} \cos(gl_g) & \frac{1}{g}\sin(gl_g) \\ -g\sin(gl_g) & \cos(gl_g) \end{pmatrix}\begin{pmatrix} 1 & 0 \\ 0 & \frac{n_o}{n_g} \end{pmatrix}\begin{pmatrix} 1 & l_0 \\ 0 & 1 \end{pmatrix}\begin{pmatrix} 1 & 0 \\ 0 & \frac{n_f}{n_o} \end{pmatrix}$$

$$z_w = \frac{n_s\left[\left(1+\left(\frac{a_o l_o}{n_o}\right)^2 - \left(\frac{a_o}{n_g g}\right)^2\right)\sin(2gl_g) - 2\frac{a_o^2 l_o}{n_o n_g g}\cos(2gl_g)\right]}{2n_g g\left[\sin^2(gl_g) + \left(\frac{a_o}{n_o n_g g}\right)^2(n_o\cos(gl_g) - n_g gl_o\sin(gl_g))^2\right]}$$

$$w_s = \frac{a_o w_o}{n_g g\sqrt{\sin^2(gl_g) + \left(\frac{a_o}{n_o n_g g}\right)^2(n_o\cos(gl_g) - n_g gl_o\sin(gl_g))^2}}$$

where, the ABCD matrix describes the optical element within the ray transfer matrix analysis, g is the gradient index constant, $L_g$ is the length of the grin lens, $l_0$ is the length of the spacer, $n_f$ is the refractive index of the optical fiber, $n_0$ is the refractive index of the spacer between the grin lens and optical fiber, $n_g$ is the index of refraction at the center of the grin lens, $n_1$ is the refractive index of the prism, $l_1$ is the length of the prism with 45 degree face, and where $n_s$ is the refractive index of the sample to be scanned, and $w_0$ is the initial bean radius from the end of the optical fiber coupled to the spacer or grin lens, $w_s$ is the beam radius, and $a_0$ is the inverse of the Rayleigh length of the initial Gaussian beam, and $z_w$ is the working distance.

In one example, having a spacer length of 0 um (also equivalent as having no spacer present), and a polymer gradient index lens with a length of 825 microns and a gradient index constant of 0.002 $mm^{-1}$, and a prism made from BK7 glass with a leg length of 300 microns and refractive index of 1.5037, results in having an imaging probe with a working distance of approximately 1090.11 microns, a confocal parameter of 2771.13 microns, and a beam waist diameter (spot size) of 40.77 microns. In such example, the polymer gradient index lens may be at least approximately 200 microns (e.g., at least 180 microns±20 microns) in diameter.

Figure 39:
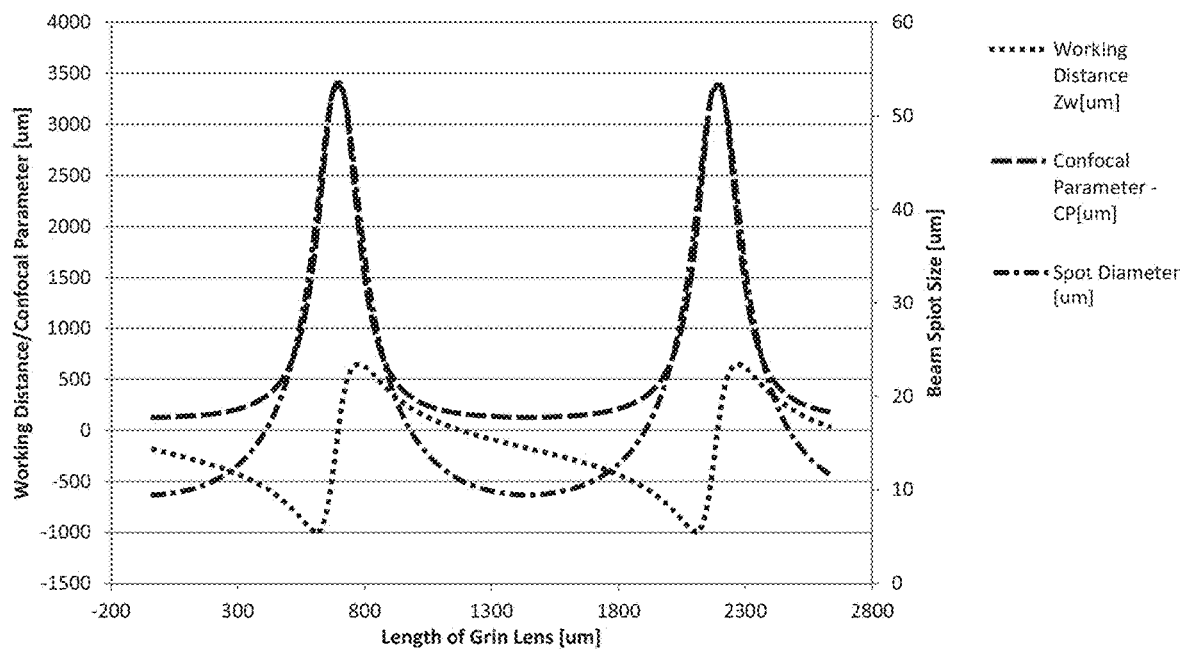
FIG. 39 is a plot showing the relationship of varying parameters in an imaging system and its effect on varying the length of a polymer gradient index lens.

FIG. 39 is a plot showing the relationship of varying the parameters in the above example and its effect on varying the length of the polymer gradient index lens. This is a plot of a grin lens design without using a spacer, and with a gradient index constant of 0.0021202 $mm^{-1}$ and plotting the grin lens length. Note that the optical parameters such as working distance, confocal parameter, and beam spot size are periodic in nature, due to the parabolic refractive index profile of the grin lens. The longest working distance and confocal parameters are achieved at approximately 748 um of grin lens length, with a confocal parameter of approximately 3400 um, and a beam spot size of approximately 23 um.

In another example, having a spacer length of 250 microns and having a refractive index of 1.037, and a polymer gradient index lens with a length of 600 microns and a gradient index constant of 0.002 $mm^{-1}$, and a prism made from BK7 glass with a leg length of 300 microns and refractive index of 1.5037, results in having an imaging probe with a working distance of approximately 1361.46 microns, a confocal parameter of 2307.13 microns, and a beam waist diameter (spot size) of 37.20 microns. In such example, the polymer gradient index lens may be at least approximately 200 microns (e.g., at least 180 microns±20 microns) in diameter.

Figure 38:
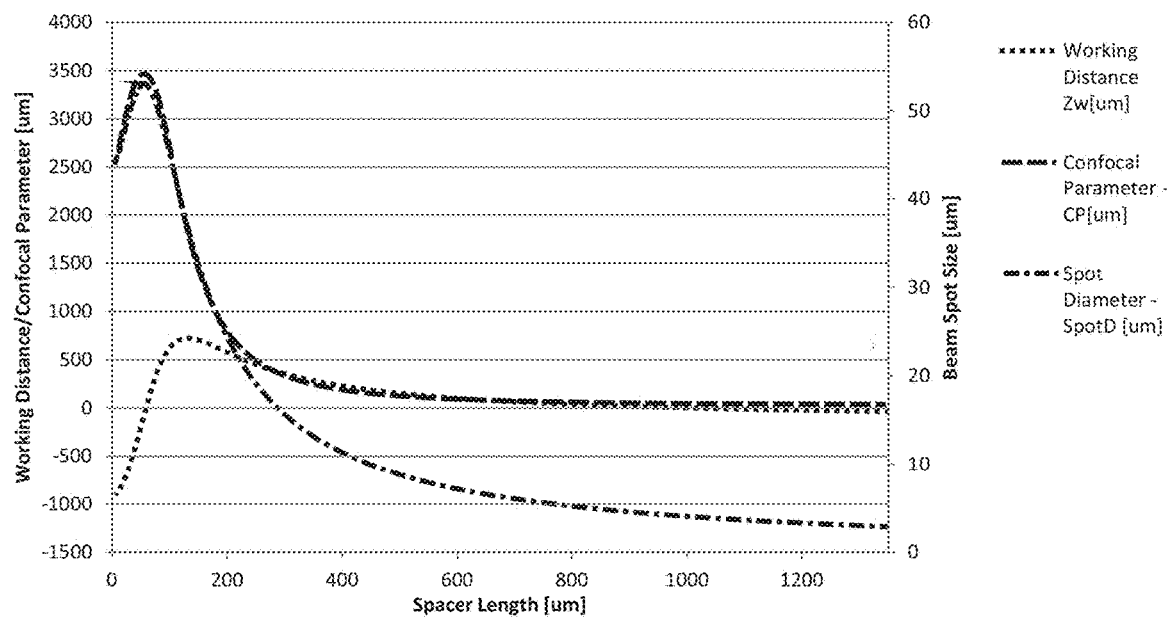
FIG. 38 is a plot showing the relationship of varying parameters in an imaging system and its effect on varying the length of a spacer.

FIG. 38 is a plot showing the relationship of varying the parameters in the above example and its effect on varying the length of the spacer. In particular, this graph shows the optimal spacer length such that the working distance is optimized to be the longest, when a grin lens of gradient index constant of 0.002102 mm$^{-1}$ is used with a length of 850 um. The spacer length is varied and plotted. The longest working distance results from the spacer being approximately 170 um long. The confocal parameter is approximately 3400 um, with a focal spot size of approximately 55 um. Note that for smaller spot sizes (higher transverse resolution), the working distance and confocal parameter may be shortened to achieve a smaller spot size.

Figure 40:
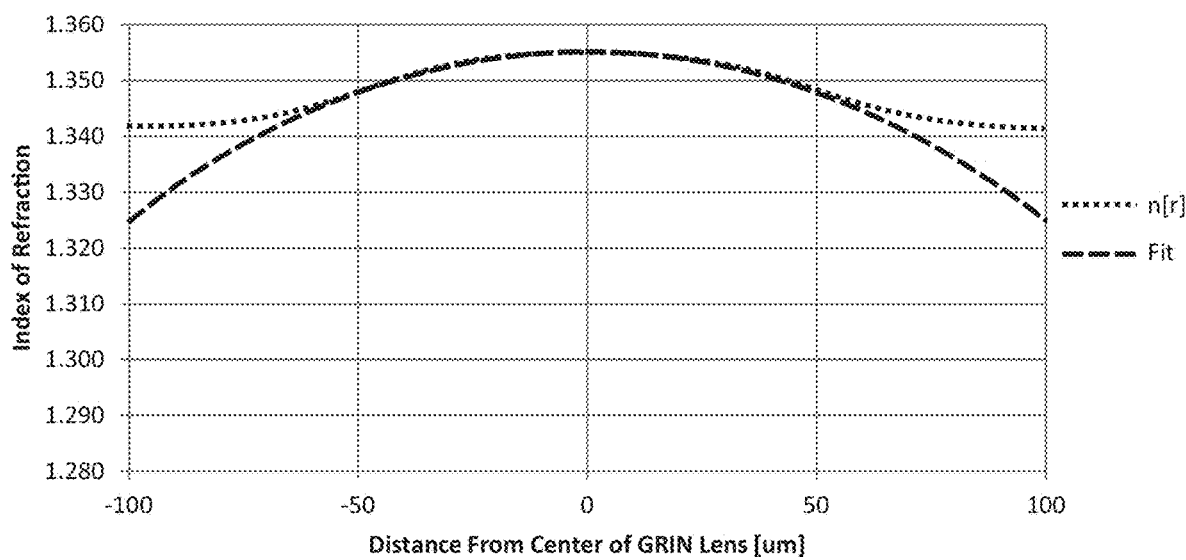
FIG. 40 is a plot of the refractive index profile of a polymer grin lens in accordance with some embodiments.

FIG. 40 is a plot of the refractive index profile of a polymer grin lens as measured with an optical fiber refractive index profiler. The zero on the horizontal axis of the graph represents the central axis of the grin lens, covering a total of 200 um in diameter. The plot includes the actual measured data, along with the parabolic curve fit that results in a gradient index constant of 0.0021202 mm$^{-1}$.

It should be noted that the imaging probe 1 is not limited to the examples of the configuration of lenses described previously, and that the imaging probe 1 may have other types of lenses and/or other combination of optical components in other embodiments. For example, in other embodiments, in addition to, or instead of, any of the above optical components, the imaging probe 1 may include axicons, phase mask lenses, Fresnel lenses, aspheric lenses, or combination thereof, to process light in a desired manner (such as focusing, defocusing, collimation, filtering, etc.). Thus, in any of the embodiments of the imaging probe 1 described herein, the optical components may have different configurations (e.g., shape, size, location, arrangement, etc.).

In one or more embodiments described herein, the motor 402, or component(s) of the motor 402 (such as a rotor), may be implemented inside the probe 1. Medical devices with internal rotor have been described in U.S. patent application Ser. Nos. 13/006,390 and 13/006,404, the disclosures of both of which are expressly incorporated by reference herein.

Also, in further embodiments, the imaging probe 1 may be used outside the medical field. For example, in other embodiments, the imaging probe 1 may be an industrial inspection probe. In such cases, the probe 1 may be used to examine and ablate materials inside narrow passage ways, such as machine bores and holes, or to perform inspection of different objects.

Also, it should be noted that although embodiments of the probe 1 have been described as having imaging capability, in other embodiments, the probe 1 may be configured to perform treatment. For example, in other embodiments, the light beam provided by the probe 1 may have an energy level that is sufficient to treat tissue (e.g., for ablation). Also, in other embodiments, instead of coupling one or more optical components to the motor 402, the probe 1 may include an energy delivery device that is coupled to the motor 402, thereby allowing the energy delivery device to be rotated by the motor 402. By means of non-limiting examples, the energy delivery device may be an ultrasound transducer, a heat emitting device, etc.

Although particular embodiments have been shown and described, it will be understood that they are not intended to limit the claimed inventions, and it will be obvious to those skilled in the art that various changes and modifications may be made without departing from the spirit and scope of the claimed inventions. The specification and drawings are, accordingly, to be regarded in an illustrative rather than restrictive sense. The claimed inventions are intended to cover alternatives, modifications, and equivalents.

What is claimed:

1. An imaging device, comprising:
a grin lens having a proximal end and a distal end, wherein at least an interior region of the grin lens is made from a polymeric material;
an optical fiber having a distal end coupled to the proximal end of the grin lens;
a beam director coupled to the distal end of the grin lens, wherein the beam director is configured to direct light at an angle relative to a longitudinal axis of the optical fiber;
a housing surrounding the beam director and having an optical port, wherein the optical port has a geometry for allowing a first light ray from inside the housing to pass therethrough to exit the housing along a first direction, and a second light ray from inside the housing to pass therethrough to exit the housing along a second direction that is opposite the first direction; and
a tube surrounding the optical fiber, wherein an interior surface of the tube is in contact with a segment of the optical fiber that is between ends of the optical fiber.

2. The imaging device of claim 1, wherein the grin lens and the optical fiber are secured relative to each other by an adhesive.

3. The imaging device of claim 1, wherein the grin lens and the optical fiber are secured relative to each other by fusion splicing.

4. The imaging device of claim 1, further comprising a spacer disposed between the distal end of the optical fiber and the grin lens, wherein the distal end of the optical fiber is indirectly coupled to the proximal end of the grin lens.

5. The imaging device of claim 1, wherein the grin lens and the optical fiber are secured relative to each other by a ferrule.

6. The imaging device of claim 5, wherein the ferrule comprises a first lumen for accommodating the distal end of the optical fiber, and a second lumen for accommodating at least a part of the grin lens.

7. The imaging device of claim 5, wherein the ferrule is made from an adhesive disposed around the distal end of the optical fiber, around at least a part of the grin lens, or around both.

8. The imaging device of claim 5, wherein a distal portion of the ferrule has a cross sectional dimension that is larger than a cross sectional dimension of the tube.

9. The imaging device of claim 5, wherein a distal portion of the ferrule has a cross sectional dimension that is a same as a cross sectional dimension of the tube.

10. The imaging device of claim 5, wherein a distal portion of the ferrule has a cross sectional dimension that is less than a cross sectional dimension of the tube.

11. The imaging device of claim 1, wherein the distal end of the optical fiber has a cross sectional dimension that is larger than a cross sectional dimension of a proximal section of the optical fiber.

12. The imaging device of claim 1, further comprising a shaft.

13. The imaging device of claim 12, wherein the grin lens has a cross sectional dimension that is a same as a cross sectional dimension of the shaft.

14. The imaging device of claim 12, wherein the grin lens has a cross sectional dimension that is larger than a cross sectional dimension of the shaft.

15. The imaging device of claim 12, wherein the grin lens has a cross sectional dimension that is less than a cross sectional dimension of the shaft.

16. The imaging device of claim 12, wherein the shaft comprises a plurality of cutouts, at least some of the cutouts at the shaft being proximal to the distal end of the optical fiber, wherein the at least some of the cutouts are distributed along an axial length of the shaft, and wherein the at least some of the cutouts comprise a first cutout and a second cutout that are completely separated from each other, the first cutout and the second cutout being on a same longitudinal side of the shaft.

17. The imaging device of claim 1, wherein the grin lens is configured to perform light collimation and light focusing.

18. An OCT system comprising the imaging device of claim 1 and a catheter body, wherein the optical fiber is configured to rotate in a lumen within the catheter body.

* * * * *